United States Patent [19]

Kajioka et al.

[11] Patent Number: 4,909,833
[45] Date of Patent: Mar. 20, 1990

[54] Δ²-1,2,4-TRIAZOLIN-5-ONE DERIVATIVES, AND USES THEREOF

[75] Inventors: Mitsuru Kajioka, Sakai; Atsushi Tsushima, Kawachinagano; Yoichi Hachitani, Hashimoto; Kenichi Ikeda, Chiba, all of Japan

[73] Assignee: Nihon Nohyaku Co., Ltd., Tokyo, Japan

[21] Appl. No.: 106,599

[22] Filed: Oct. 13, 1987

Related U.S. Application Data

[62] Division of Ser. No. 845,867, Mar. 28, 1986.

[30] Foreign Application Priority Data

Oct. 26, 1985 [JP] Japan .................... 60-239999

[51] Int. Cl.⁴ .................... A01N 43/64; C07D 249/12
[52] U.S. Cl. .................... 71/92; 548/263.2
[58] Field of Search .................... 548/263, 265; 71/92, 71/106

[56] References Cited

U.S. PATENT DOCUMENTS

| | | | |
|---|---|---|---|
| 4,318,731 | 3/1982 | Kajioka et al. | 71/92 |
| 4,398,943 | 8/1983 | Kajioka et al. | 71/92 |
| 4,806,145 | 2/1989 | Marooetz | 71/92 |

FOREIGN PATENT DOCUMENTS

| | | | |
|---|---|---|---|
| 57-181069 | 1/1982 | Japan | 548/263 |
| 2162511 | 2/1986 | United Kingdom | 548/263 |

*Primary Examiner*—Glennon H. Hollrah
*Assistant Examiner*—Patricia L. Morris
*Attorney, Agent, or Firm*—Cushman, Darby & Cushman

[57] ABSTRACT

A Δ²-1,2,4-triazolin-5-one derivative represented by the following general formula (I), a process for manufacturing thereof, a herbicidal composition comprising it as an active ingredient, and a use of it as a herbicide:

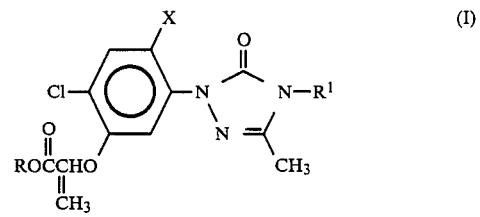

wherein R is a hydrogen atom, a univalent alkali metal atom, an unsubstituted quaternary ammonium salt, a substituted quaternary ammonium salt having at least one $C_1$–$C_4$ alkyl group as a substituent, an unsubstituted-alkyl group having 1 to 6 carbon atoms, a $C_1$–$C_6$ substituted-alkyl group having at least one halogen atom as a substituent, a cycloalkyl group having 3 to 6 carbon atoms, a $C_1$–$C_3$ substituted-alkyl group having a cyano group as a substituent, an alkenyl group having 2 to 6 carbon atoms, an alkynyl group having to 2 to 6 carbon atoms, an alkoxyalkyl group having 2 to 6 carbon atoms, an alkylthioalkyl group having to 2 to 8 carbon atoms, an alkylsulfinylalkyl group having 2 to 6 carbon atoms, an alkylsulfonylalkyl group having 2 to 6 carbon atoms, an alkoxyalkoxyalkyl group having 3 to 8 carbon atoms, a hydroxycarbonylalkyl group having 2 to 3 carbon atoms, an alkoxycarbonylalkyl group having 3 to 6 carbon atoms, an unsubstituted-benzyl group, a substituted-benzyl group having at least one substituent selected from the group consisting of halogen atoms and alkyl groups having 1 to 3 carbon atoms, or a phenethyl group; $R^1$ is a haloalkyl group having 2 to 5 carbon atoms; and X is a halogen atom.

14 Claims, No Drawings

$\Delta^2$-1,2,4-TRIAZOLIN-5-ONE DERIVATIVES, AND USES THEREOF

This is a division of application Ser. No. 845,867, filed Mar, 29, 1986.

BACKGROUND OF THE INVENTION

Field of the Invention

This invention relates to $\Delta^2$-1,2,4-triazolin-5-one derivatives represented by the general formula (I):

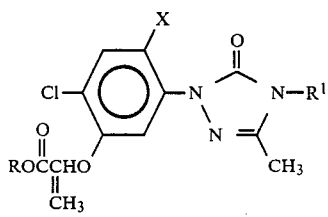

(wherein R is a hydrogen atom, a univalent alkali metal atom, an unsubstituted quaternary ammonium salt, a substituted quaternary ammonium salt having at least one $C_1$-$C_4$ alkyl group as a substituent, an unsubstituted-alkyl group having 1 to 6 carbon atoms, a $C_1$-$C_6$ substituted-alkyl group having at least one halogen atom as a substituent, a cycloalkyl group having 3 to 6 carbon atoms, a $C_1$-$C_3$ substituted-alkyl group having a cyano group as a substituent, an alkenyl group having 2 to 6 carbon atoms, an alkynyl group having 2 to 6 carbon atoms, an alkoxyalkyl group having 2 to 6 carbon atoms, an alkylthioalkyl group having 2 to 8 carbon atoms, an alkylsulfinylalkyl group having 2 to 6 carbon atoms, an alkylsulfonylalkyl group having 2 to 6 carbon atoms, an alkoxyalkoxyalkyl group having 3 to 8 carbon atoms, a hydroxycarbonylalkyl group having 2 to 3 carbon atoms, an alkoxycarbonylalkyl group having 3 to 6 carbon atoms, an unsubstituted-benzyl group, a substituted-benzyl group having at least one substituent selected from the group consisting of halogen atoms and alkyl groups having 1 to 3 carbon atoms, or a phenethyl group; $R^1$ is a haloalkyl group having 2 to 5 carbon atoms; and X is a halogen atom), a process for production thereof, and uses thereof.

DESCRIPTION OF THE PRIOR ART

The present inventors have found that compound represented by the above general formula (I) are useful as agricultural chemicals, in particular, herbicides.

Compounds similar to the compounds of this invention are disclosed in Japanese Patent Kokai (Laid-open) No. Sho 57-181069 (1982), U.S. Pat. No. 4,318,731, U.S. Pat. No. 4,398,943, U.S. Pat. No. 4,404,019, WO85/01637 and WO85/04307. For example, U.S. Pat. No. 4,318,731 discloses a compound represented by the formula,

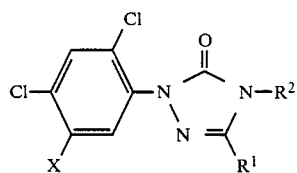

wherein, $R^1$ is a $C_1$-$C_4$ alkyl; $R^2$ is a hydrogen atom, a $C_1$-$C_4$ alkyl group, or a $C_2$-$C_4$ alkenyl group; and X is a hydroxy group, a $C_1$-$C_4$ alkyl group, a $C_1$-$C_6$ alkyloxy group, an alkyloxyalkyloxy group of which two alkyls may be same as or different from each other and each alkyl is of $C_1$-$C_4$, a $C_2$-$C_4$ alkenyloxy, or an alkyloxycarbonyl-alkyloxy group of which two alkyls may be same as or different from each other and each alkyl is of $C_1$-$C_4$; U.S. Pat. No. 4,398,943 discloses a compound represented by the formula,

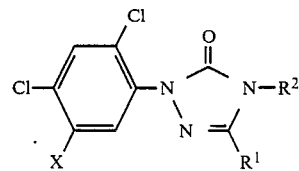

wherein $R^1$ is an alkyl group; $R^2$ is an alkynyl group, a halomethyl group, or a haloethyl group; and X is an alkoxy group, an alkenyloxy group, an alkoxy-alkoxy group, an alkynyloxy group, a hydroxy group, a halomethyloxy group, or a haloethyloxy group; and U.S. Pat. No. 4,404,019 discloses a compound represented by the formula,

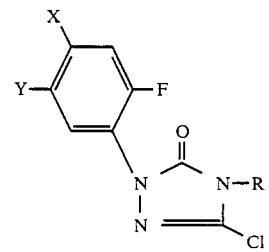

wherein R is a $C_1$-$C_4$ alkyl group, a $C_3$-$C_4$ alkenyl group or a $C_3$-$C_4$ cycloakyl group, X is a chlorine atom or a bromine atom and Y is a hydrogen atom or a $C_1$-$C_4$ alkoxy group, which is useful as a herbicide.

Those compounds, however, can not be considered as suitable herbicides from the viewpoints of the dosage and their effects. Furthermore, WO 85/01637 discloses a compound represented by the following formula,

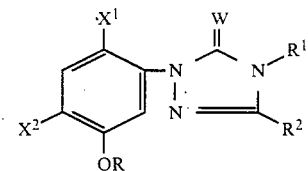

in which $X^1$ and $X^2$ are independently selected from halogen, haloalkyl, and alkyl;

W is oxygen or sulfur;

R is a three- to eight-membered ring heterocyclic group of one or two, same or different, ring heteroatoms selected from oxygen, sulfur, and nitrogen or an alkyl radical substituted with said heterocyclic group, said heterocyclic group being unsubstituted or substituted with one or more substituents selected from halogen, alkyl, and haloalkyl, or said heterocyclic group being adjoined to a benzene ring at two adjacent ring carbon atoms to form a benzo-heterocycle bicyclic group, said sulfur heteroatom being present in divalent form, S-oxide form, or S-dioxide form;

$R^1$ is alkyl, haloalkyl, cyanoalkyl, alkenyl, alkynyl, or a group of the formula -alkyl-Y-$R^3$;

$R^2$ is halogen, alkyl, cyanoalkyl, haloalkyl, arylalkyl, or a group of the formula -alkyl-Y-$R^3$;

$R^3$ is alkyl, alkenyl, or alkynyl; and

Y is oxygen or $S(O)_r$ in which r is 0 to 2; however, the compound disclosed needs a relatively high dosage for the control of the undersirable weeds and does not have sufficient selectivites between the useful crops and the undersible weeds. WO85/04307 discloses also a similar compound represented by the following formula,

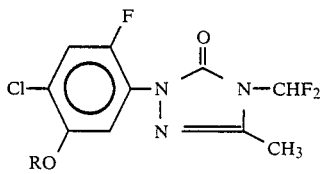

in which R is a radical selected from 2-propynyl, 1-methylethyl-2-propynyl, methoxymethyl, 2-propenyl, and 1-methyl-2-methoxyethyl. The compound disclosed, however, kills useful crops in addition to weeds if it is used at a relatively high dosage. On the other hand, sufficient controlling effects of weeds can not be expected if it is used at a relatively lower dosage at which it still gives certain but evident damages on the crops. That is, the compound fails to show sufficient selectivities between the useful crops and weeds. Therefore, there is still a strong demand for a herbicide capable of controlling weeds without causing substantial damages on crops at a lower dosage. While, the present inventors have found that the compounds of this invention disclosed in neither those prior arts nor in any literatures can meet such demand.

Additionally, the present inventors have found that surprisingly, the compounds of this invention exhibit excellent herbicidal activities in a lower dosage and have lower phytotoxicities as compared with the compounds disclosed in the above-mentioned prior art references, whereby this invention has been accomplished.

An object of the present invention is to provide a compound having excellent herbicidal activities and only low phytotoxicities.

A further object of the present invention is to provide a herbicidal composition comprising an effective amount of a compound having excellent herbicidal activities and high crop safety represented by said general formula (I), and suitable inert carrier.

A further object of the present invention is to provide a herbicidal composition comprising said compound which is very useful not only as a pre-emergence treatment type herbicide, but also as a post-emergence treatment type herbicide for upland crops. A further object of the present invention is to provide a method of treating said compound as herbicide for upland crops.

Further objects of the invention will become apparent from the description of the invention which follows.

Preferable examples of the substituent R of the compounds represented by the general formula (I) include, for example, hydrogen atom; univalent alkali metal atoms such as Na, K and the like; quaternary ammonium salts of ammonium, mono-, di-, tri- or tetramethylammonium, mono-, di-, tri- or tetraethylammonium, mono-, di-, tri- or tetrapropylammonium, mono-, di-, tri- or tetrabutylammonium, and the like; alkyl groups such as methyl, ethyl, n-propyl, isopropyl, n-butyl, isobutyl, sec-butyl, t-butyl, pentyl, hexyl, and the like; substituted-alkyl groups having halogen atoms as the substituents such as chloromethyl, bromomethyl, chloroethyl, bromoethyl, chloropropyl, bromopropyl, chlorobutyl, bromobutyl, chloropentyl, bromopentyl, chlorohexyl, bromohexyl, and di-, tri- or polyhaloalkyl thereof and the like; cycloalkyl groups such as cyclopropyl, cyclopentyl, cyclohexyl, and the like; substituted alkyl groups having a cyano group as the substituent such as cyanomethyl, cyanoethyl, cyanopropyl, and the like; alkenyl groups such as ethenyl, 2-propenyl, 1-methylpropenyl, 1,1-dimethylpropenyl, 2-butenyl, pentenyl, hexenyl, and the like; alkynyl groups such as ethynyl, 2-propynyl, 1-methylpropynyl, 1,1-dimethylpropynyl, 2-butynyl, pentynyl, hexynyl, and the like; alkoxyalkyl groups such as methoxymethyl, ethoxymethyl, propoxymethyl, butoxymethyl, pentyloxymethyl, methoxyethyl, ethoxyethyl, propoxyethyl, butoxyethyl, methoxypropyl, ethoxypropyl, propoxypropyl, methoxybutyl, ethoxybutyl, methoxypentyl, and the like; alkylthioalkyl groups such as methylthiomethyl, ethylthiomethyl, propylthiomethyl, butylthiomethyl, pentylthiomethyl, hexylthiomethyl, heptylthiomethyl, methylthioethyl, ethylthioethyl, propylthioethyl, butylthioethyl, pentylthioethyl, hexylthioethyl, methylthiopropyl, ethylthiopropyl, propylthiopropyl, butylthiopropyl, pentylthiopropyl, methylthiobutyl, ethylthiobutyl, propylthiobutyl, butylthiobutyl, methylthiopentyl, ethylthiopentyl, propylthiopentyl, methylthiohexyl, ethylthiohexyl, methylthioheptyl, and the like; alkylsulfinylalkyl groups such as methylsulfinylmethyl, ethylsulfinylmethyl, propylsulfinylmethyl, butylsulfinylmethyl, pentylsulfinylmethyl, methylsulfinylethyl, ethylsulfinylethyl, propylsulfinylethyl, butylsulfinylethyl, methylsulfinylpropyl, ethylsulfinylpropyl, propylsulfinylpropyl, methylsulfinylbutyl, ethylsulfinylbutyl, methylsulfinylpentyl, and the like; alkylsulfonylalkyl groups such as methylsulfonylmethyl, ethylsulfonylmethyl, propylsulfonylmethyl, butylsulfonylmethyl, pentylsulfonylmethyl, methylsulfonylethyl, ethylsulfonylethyl, propylsulfonylethyl, butylsulfonylethyl, methylsulfonylpropyl, ethylsulfonylpropyl, propylsulfonylpropyl, methylsulfonylbutyl, ethylsulfonylbutyl, methylsulfonylpentyl, and the like; alkoxyalkoxyalkyl groups such as methoxymethoxymethyl, ethoxymethoxymethyl, propoxymethoxymethyl, butoxymethoxymethyl, pentyloxymethoxymethyl, hexyloxymethoxymethyl, methoxyethoxyethyl, ethoxyethoxyethyl, propoxyethoxyethyl, butoxyethoxyethyl, and the like; hydroxycarbonylalkyl groups such as hydroxycarbonylmethyl, hydroxycarbonylethyl, and the like; alkoxycarbonylalkyl groups such as methoxycarbonylmethyl, ethoxycarbonylmethyl, propoxycarbonylmethyl, butoxycarbonylmethyl, methoxycarbonylethyl, ethoxycarbonylethyl, propoxycarbonylethyl, and the like; a benzyl group; substituted benzyl groups such as chlorobenzyl groups having the substituent in the o-, m-or p-position, bromobenzyl groups having the substituent in the o-, m-or p-position, ethylbenzyl groups having the substituent in the o-, m- or p-position, propylbenzyl groups having the substituent in the o-, m-or p-position, and the like; an α-methylbenzyl group; a phenethyl group; etc. As a preferable substituent for $R^1$, there can be exemplified haloalkyl groups such as 2-chloro-1,1,2-trifluoroethyl, 1,1,2,2-tetrafluoroethyl, 2,2,2-trifluoroethyl, 3-chloropropyl, 3-bromopropyl, 3-fluoropropyl, 2,2-difluoropropyl, 1,1,2,3,3,3-hexafluoropropyl, 4-chlorobutyl, 4-fluorobutyl, 5-chlorobutyl, 5-fluorobutyl, and the like.

DESCRIPTION OF THE PREFERRED EMBODIMENTS

As to a process for producing the compound represented by the general formula (I) of this invention, it can be produced, for example, by the following process:

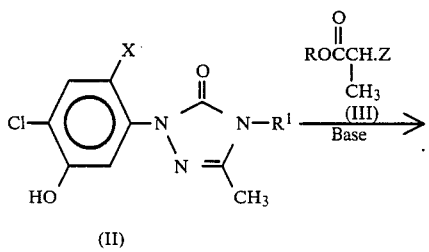

wherein R, R¹ and X have the same meanings as defined above, and Z is a halogen atom.

That is to say, the compound of the general formula (I) can be obtained by reacting a compound represented by the general formula (II) with a compound represented by the general formula (III) in the presence of an inert solvent.

As the inert solvent used in the reaction of this invention, any one may be used so long as it does not inhibit the progress of such a rection greatly. There can be exemplified, for example, aromatic hydrocarbons such as benzene, toluene, xylene and the like; aliphatic hydrocarbons such as n-hexane, cyclohexane and the like; alcohols such as methanol, ethanol, propanol, glycol and the like; ketones such as acetone, methyl ethyl ketone, cyclohexanone and the like; lower fatty acid esters such as ethyl acetate and the like; ethers such as tetrahydrofuran, dioxane and the like; lower fatty acid amides such as dimethylformamide, dimethylacetamide and the like; water; dimethylsulfoxide; etc.

These solvents are used alone or as a mixture thereof.

As the base usable in this invention, there can be exemplified, for example, inorganic bases such as sodium carbonate, sodium hydride, potassium carbonate, sodium hydrogencarbonate, potassium hydrogencarbonate, sodium hydroxide, potassium hydroxide, alcoholates of alkali metals and the like; and organic bases such as pyridine, trimethylamine, triethylamine, diethylaniline, 1,8-diazabicyclo-[5,4,0]-7-undecene and the like.

The reaction of this invention can be carried out at a temperature properly selected, for example, in the range of 0° C. to 150° C.

Although the reaction of the compounds in each reaction path is an equimolar reaction, either of the compounds may be added in a slight excess.

The reaction time is selected preferably in the range of 0.5 to 48 hours.

After completion of the reaction, the desired compound can be collected by treating the reaction product by a conventional method.

The compound of the general formula (I) can be produced also according to the following formulas:

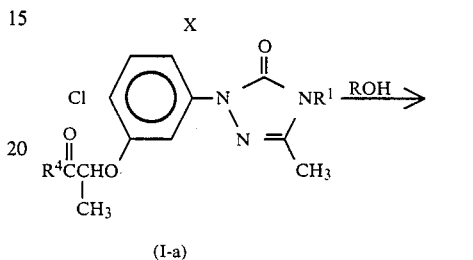

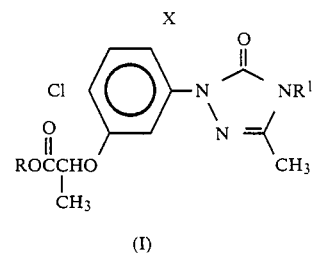

wherein R, R¹ and X have the same meanings as defined above, and R⁴ is a hydroxyl group or a halogen atom.

That is to say, the compound of the general formula (I) can be obtained by reacting a compound represented by the general formula (I-a) with the corresponding alcohol.

A compound of the general formula (I) in which R is a lower alkylsulfinylalkyl group or a lower alkylsulfonylalkyl group can be obtained also by oxydizing a compound of the general formula (I) in which R is a lower alkylthioalkyl group by using a suitable oxidizing agent.

Typical examples of the compounds of the general formula (I) are as shown in Table 1.

General formula (I):

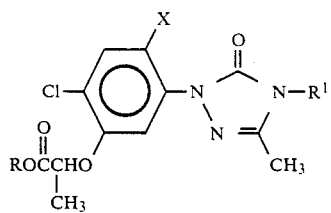

TABLE 1

| Compound No. | R | R¹ | X | Physical properties |
|---|---|---|---|---|
| 1 | H | $CF_2CHF_2$ | Cl | $n_D^{24}$ 1.5200 |
| 2 | H | $CF_2CHClF$ | Cl | NMR: $\delta_{TMS}^{CDCl_3}$ (ppm) 1.65 (d, 3H), 2.40 (t, 3H), 4.70 (q, |

TABLE 1-continued

| Compound No. | R | R¹ | X | Physical properties |
|---|---|---|---|---|
| | | | | 1H), 6.95 (s, 1H), 7.50 (s, 1H), 6.70–7.80 (m, 1H), 9.00 (s, 1H) |
| 3 | H | $CF_2CHF_2$ | F | $n_D^{24}$ 1.5079 |
| 4 | H | $CF_2CClF$ | F | m.p. 107.8° C. |
| 5 | H | $CH_2CF_3$ | F | m.p. 180.9° C. |
| 6 | Na | $CF_2CHF_2$ | Cl | m.p. 141.8° C. |
| 7 | Na | $CF_2CHF_2$ | F | m.p. 178.9° C. |
| 8 | Na | $CF_2CHClF$ | F | m.p. 145.8° C. |
| 9 | K | $CF_2CHF_2$ | Cl | m.p. 201.4° C. |
| 10 | K | $CF_2CHF_2$ | F | m.p. 103.3° C. |
| 11 | $(n-C_4H_9)_2NH_2$ | $CF_2CHF_2$ | Cl | m.p. 192.8° C. |
| 12 | $(n-C_4H_9)_2NH_2\cdot$ | $CF_2CHF_2$ | F | m.p. 171.0° C. |
| 13 | $CH_3$ | $CF_2CHF_2$ | Cl | $n_D^{24}$ 1.5072 |
| 14 | $CH_3$ | $CF_2CHClF$ | Cl | $n_D^{23}$ 1.5262 |
| 15 | $CH_3$ | $CF_2CHF_2$ | F | $n_D^{23}$ 1.4977 |
| 16 | $C_2H_5$ | $CF_2CHF_2$ | Cl | $n_D^{23}$ 1.5039 |
| 17 | $C_2H_5$ | $CH_2CF_3$ | Cl | $n_D^{22}$ 1.5150 |
| 18 | $C_2H_5$ | $CF_2CHF_2$ | F | $n_D^{24}$ 1.4891 |
| 19 | $C_2H_5$ | $CH_2CF_3$ | F | $n_D^{19.5}$ 1.5030 |
| 20 | $C_2H_5$ | $CF_2CHClF$ | F | $n_D^{22}$ 1.5062 |
| 21 | $n-C_3H_7$ | $CF_2CHF_2$ | Cl | $n_D^{23}$ 1.4998 |
| 22 | $s-C_4H_9$ | $CF_2CHClF$ | F | $n_D^{23}$ 1.4985 |
| 23 | $n-C_6H_{13}$ | $CF_2CHF_2$ | Cl | $n_D^{23}$ 1.4940 |
| 24 | $n-C_6H_{13}$ | $CF_2CHF_2$ | F | $n_D^{26}$ 1.4832 |
| 25 | $Cl(CH_2)_2$ | $CF_2CHF_2$ | Cl | $n_D^{24}$ 1.5161 |
| 26 | $Cl(CH_2)_2$ | $CF_2CHClF$ | Cl | $n_D^{23}$ 1.5253 |
| 27 | $Cl(CH_2)_2$ | $CF_2CHF_2$ | F | $n_D^{18}$ 1.5049 |
| 28 | $Br(CH_2)_2$ | $CF_2CHF_2$ | Cl | $n_D^{24}$ 1.5229 |
| 29 | $Br(CH_2)_2$ | $CF_2CHF_2$ | F | $n_D^{26}$ 1.5092 |
| 30 | $Br(CH_2)_2$ | $CF_2CHClF$ | F | $n_D^{23}$ 1.5194 |
| 31 | $Cl(CH_2)_3$ | $CF_2CHF_2$ | Cl | $n_D^{24}$ 1.5139 |
| 32 | $Cl(CH_2)_3$ | $CF_2CHF_2$ | F | m.p. 48.5° C. |
| 33 | $Cl(CH_2)_3$ | $CF_2CHClF$ | F | $n_D^{23}$ 1.5102 |
| 34 | $Cl(CH_2)_3$ | $CH_2CF_3$ | F | m.p. 89.3° C. |
| 35 | $Br(CH_2)_3$ | $CF_2CHF_2$ | Cl | $n_D^{24}$ 1.5211 |
| 36 | $Br(CH_2)_3$ | $CF_2CHClF$ | Cl | $n_D^{23}$ 1.5293 |
| 37 | $Br(CH_2)_3$ | $CF_2CHF_2$ | F | $n_D^{26}$ 1.5088 |
| 38 | $Cl(CH_2)_4$ | $CF_2CHF_2$ | Cl | $n_D^{24}$ 1.5135 |
| 39 | $Cl(CH_2)_4$ | $CF_2CHF_2$ | F | $n_D^{18}$ 1.5012 |
| 40 | $Cl(CH_2)_4$ | $CF_2CHClF$ | F | $n_D^{23}$ 1.5089 |
| 41 | cyclopentyl-H | $CF_2CHF_2$ | F | m.p. 62.5° C. |
| 42 | cyclopentyl-H | $CF_2CHClF$ | F | $n_D^{22}$ 1.5102 |
| 43 | cyclohexyl-H | $CF_2CHF_2$ | Cl | $n_D^{28}$ 1.5058 |
| 44 | cyclohexyl-H | $CF_2CHClF$ | Cl | $n_D^{23}$ 1.5268 |
| 45 | cyclohexyl-H | $CF_2CHF_2$ | F | $n_D^{26}$ 1.4965 |
| 46 | cyclohexyl-H | $CH_2CF_3$ | F | $n_D^{19.5}$ 1.5059 |
| 47 | $NCCH_2CH_2$ | $CF_2CHF_2$ | Cl | $n_D^{24}$ 1.5075 |

TABLE 1-continued

| Compound No. | R | R¹ | X | Physical properties |
|---|---|---|---|---|
| 48 | NCCH$_2$CH$_2$ | CF$_2$CHF$_2$ | F | m.p. 83.8° C. |
| 49 | CH$_2$=CHCH$_2$ | CF$_2$CHF$_2$ | Cl | n$_D^{28}$ 1.5084 |
| 50 | CH$_2$=CHCH$_2$ | CF$_2$CHClF | Cl | n$_D^{23}$ 1.5262 |
| 51 | CH$_2$=CHCH$_2$ | CF$_2$CHF$_2$ | F | n$_D^{26}$ 1.4964 |
| 52 | CH$_2$=CHCH$_2$ | CH$_2$CF$_3$ | F | n$_D^{19.9}$ 1.5122 |
| 53 | CH≡CCH$_2$ | CF$_2$CHF$_2$ | Cl | n$_D^{28}$ 1.5126 |
| 54 | CH≡CCH$_2$ | CF$_2$CHF$_2$ | F | n$_D^{23}$ 1.5025 |
| 55 | CH≡CCH$_2$ | CF$_2$CHClF | F | n$_D^{22}$ 1.5130 |
| 56 | CH$_3$O(CH$_2$)$_2$ | CF$_2$CHClF | Cl | n$_D^{23}$ 1.5230 |
| 57 | CH$_3$O(CH$_2$)$_2$ | CF$_2$CHF$_2$ | F | n$_D^{19}$ 1.4939 |
| 58 | CH$_3$CH$_2$O(CH$_2$)$_2$ | CF$_2$CHF$_2$ | Cl | n$_D^{28}$ 1.4990 |
| 59 | CH$_3$CH$_2$O(CH$_2$)$_2$ | CF$_2$CHF$_2$ | F | n$_D^{26}$ 1.4875 |
| 60 | CH$_3$CH$_2$O(CH$_2$)$_2$ | CF$_2$CHClF | F | n$_D^{22}$ 1.5022 |
| 61 | n-C$_4$H$_9$O(CH$_2$)$_2$ | CF$_2$CHF$_2$ | Cl | n$_D^{28}$ 1.4944 |
| 62 | n-C$_4$H$_9$O(CH$_2$)$_2$ | CF$_2$CHF$_2$ | F | n$_D^{23}$ 1.4849 |
| 63 | CH$_3$S(CH$_2$)$_2$ | CF$_2$CHF$_2$ | Cl | n$_D^{24}$ 1.5222 |
| 64 | CH$_3$S(CH$_2$)$_2$ | CF$_2$CHF$_2$ | F | n$_D^{18}$ 1.5128 |
| 65 | CH$_3$CH$_2$S(CH$_2$)$_2$ | CF$_2$CHF$_2$ | Cl | n$_D^{24}$ 1.5197 |
| 66 | CH$_3$CH$_2$S(CH$_2$)$_2$ | CF$_2$CHClF | Cl | n$_D^{23}$ 1.5326 |
| 67 | i-C$_3$H$_7$S(CH$_2$)$_2$ | CF$_2$CHF$_2$ | Cl | n$_D^{24}$ 1.5145 |
| 68 | i-C$_4$H$_9$S(CH$_2$)$_2$ | CF$_2$CHF$_2$ | F | n$_D^{25}$ 1.5022 |
| 69 | C$_2$H$_5$S(CH$_2$)$_3$ | CF$_2$CHF$_2$ | F | n$_D^{25}$ 1.5061 |
| 70 | n-C$_4$H$_9$S(CH$_2$)$_3$ | CF$_2$CHClF | F | n$_D^{23}$ 1.5103 |
| 71 | CH$_3$SO(CH$_2$)$_2$ | CF$_2$CHF$_2$ | Cl | n$_D^{25}$ 1.5195 |
| 72 | i-C$_4$H$_9$SO(CH$_2$)$_2$ | CF$_2$CHF$_2$ | F | n$_D^{25}$ 1.5038 |
| 73 | CH$_3$CH$_2$SO$_2$(CH$_2$)$_2$ | CF$_2$CHF$_2$ | Cl | n$_D^{25}$ 1.5061 |
| 74 | i-C$_4$H$_9$SO$_2$(CH$_2$)$_2$ | CF$_2$CHF$_2$ | F | n$_D^{25}$ 1.5022 |
| 75 | C$_2$H$_5$SO$_2$(CH$_2$)$_3$ | CF$_2$CHF$_2$ | F | m.p. 122.3° C. |
| 76 | CH$_3$O(CH$_2$)$_2$O(CH$_2$)$_2$ | CF$_2$CHF$_2$ | Cl | n$_D^{28}$ 1.4982 |
| 77 | CH$_3$O(CH$_2$)$_2$O(CH$_2$)$_2$ | CF$_2$CHF$_2$ | F | n$_D^{24}$ 1.4880 |
| 78 | CH$_3$O(CH$_2$)$_2$O(CH$_2$)$_2$ | CF$_2$CHClF | F | n$_D^{22}$ 1.5005 |
| 79 | CH$_3$OC(OCH$_3$)=CH— | CF$_2$CHF$_2$ | Cl | n$_D^{19}$ 1.5027 |
| 80 | CH$_3$OC(OCH$_3$)=CH— | CF$_2$CHF$_2$ | F | n$_D^{23}$ 1.4918 |
| 81 | CH$_3$OC(OCH$_3$)=CH— | CF$_2$CHClF | F | n$_D^{23}$ 1.4989 |
| 82 | C$_6$H$_5$CH$_2$— | CF$_2$CHF$_2$ | Cl | n$_D^{25}$ 1.5325 |
| 83 | C$_6$H$_5$CH$_2$— | CF$_2$CHClF | Cl | n$_D^{23}$ 1.5389 |
| 84 | C$_6$H$_5$CH$_2$— | CF$_2$CHF$_2$ | F | m.p. 91.6° C. |
| 85 | 4-Cl-C$_6$H$_4$CH$_2$— | CF$_2$CHF$_2$ | Cl | m.p. 119.3° C. |
| 86 | 4-Cl-C$_6$H$_4$CH$_2$— | CH$_2$CF$_3$ | Cl | n$_D^{22}$ 1.5433 |
| 87 | 4-Cl-C$_6$H$_4$CH$_2$— | CF$_2$CHF$_2$ | F | n$_D^{18}$ 1.5329 |

TABLE 1-continued

| Compound No. | R | R¹ | X | Physical properties |
|---|---|---|---|---|
| 88 | Cl—⟨C₆H₄⟩—CH₂— | $CF_2CHClF$ | F | $n_D^{23}$ 1.5386 |
| 89 | $CH_3$—⟨C₆H₄⟩—CH₂— | $CF_2CHF_2$ | F | $n_D^{26}$ 1.5200 |
| 90 | ⟨C₆H₅⟩—CH₂CH₂— | $CF_2CHF_2$ | Cl | $n_D^{25}$ 1.5282 |
| 91 | ⟨C₆H₅⟩—CH₂CH₂— | $CF_2CHF_2$ | F | $n_D^{23}$ 1.5203 |

The compound of the general formula (II) can be synthesized by the following reaction path:

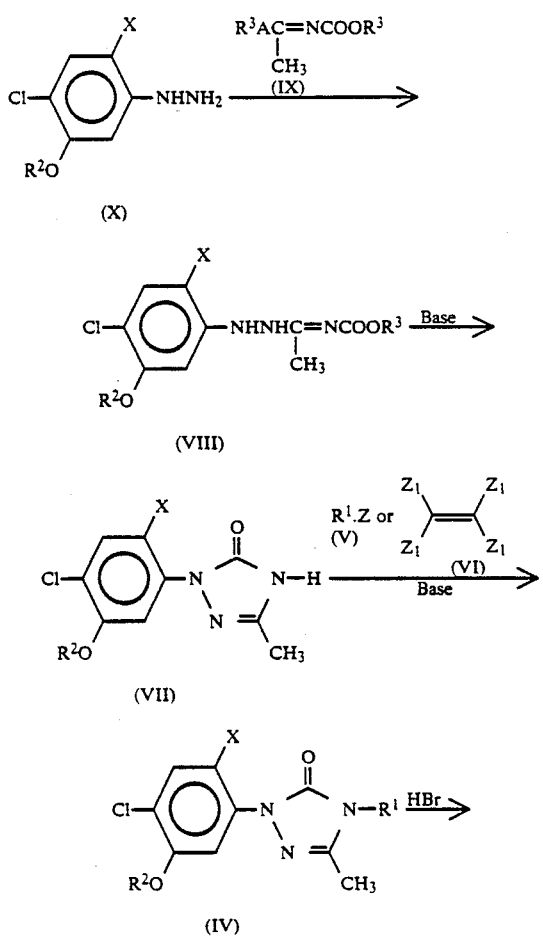

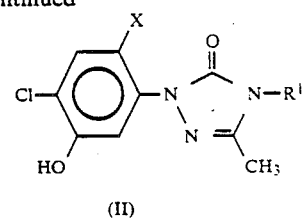

wherein $R^1$, Z and X are as defined above; each of $R^2$ and $R^3$ is a lower alkyl group; A is an oxygen atom or a sulfur atom; and $Z_1$'s which may be the same or different are halogen atoms.

In detail, the compound of the general formula (II) can be obtained by reacting a compound represented by the general formula (X) with a compound represented by the general formula (IX) with heating in an inert solvent, either isolating or not isolating the resulting compound represented by the general formula (VIII), subjecting this compound to ring closure reaction in the presence of a base to convert the same into a compound represented by the general formula (VII), reacting said compound (VII) with a halide represented by the general formula (V) or (VI) to obtain a compound represented by the general formula (IV), and reacting said compound (IV) with hydrogen bromide.

In producing the compound of the general formula (II) from the compound of the general formula (IV), hydrogen iodide or an alkyl thiolate may be used in place of hydrogen bromide.

Examples of this invention are given below not by way of limitation but by way of illustration.

EXAMPLE 1

4-(2-Chloro-1,1,2-trifluoroethyl)-1-{[2,4-dichloro-5-(1-methoxycarbonyl)ethoxy]phenyl}-3-methyl-Δ²-1,2,4-triazolin-5one (Compound No. 14)

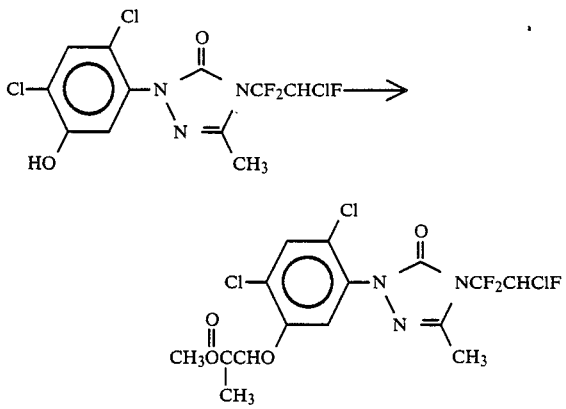

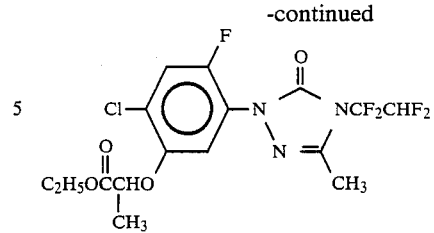

In 50 ml of methanol was dissolved 0.62 g (0.011 mole) of KOH, and 3.6 g (0.01 mole) of 4-(2-chloro-1,1,2-trifluoroethyl)-1-(2,4-dichloro-5-hydroxyphenyl)-3-methyl-$\Delta^2$-1,2,4-triazolin-5-one was added to the resulting solution to be converted into its potassium salt. Then, 1.83 g (0.011 mole) of methyl α-bromopropionate was added, and the resulting mixture was refluxed with heating for 3 hours. After completion of the reaction, the reaction mixture was poured into ice water, and the resulting mixture was extracted with ether, after which the extract was concentrated to obtain 4.0 g of the desired compound: $n_D^{23}$ 1.5262, yield 88.9%.

EXAMPLE 2

1-[4-Chloro-5-(1-ethoxycarbonyl)ethoxy-2-fluorophenyl]-3-methyl-4-(1,1,2,2-tetrafluoroethyl)-$\Delta^2$-1,2,4-triazolin-5-one (Compound No. 18)

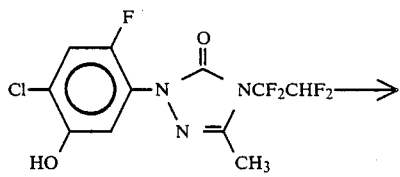

In 150 ml of acetone were suspended 9.0 g (0.026 mole) of 1-(4-chloro-2-fluoro-5-hydroxyphenyl)-3-methyl-4-(1,1,2,2-tetrafluoroethyl)-$\Delta^2$-1,2,4-triazolin-5-one, 7.9 g (0.044 mole) of ethyl α-bromopropionate and 9.0 g of potassium carbonate, and the resulting suspension was refluxed with heating for 2 hours. After completion of the reaction, the reaction suspension was cooled to room temperature. Then, the insoluble materials were removed by filtation, after which the filtrate was concentrated and the residue was purified by column chromatography to obtain 9.22 g of the desired compound.

Physical properties: $n_D^{24}$ 1.4891, yield 79.3%.

EXAMPLE 3

1-{5-[1-(3-Chloropropoxycarbonyl)ethoxy]-2,4-dichlorophenyl}-3-methyl-4-(1,1,2,2-tetrafluoroethyl)-$\Delta^2$-1,2,4-triazolin-5-one (Compound No. 31)

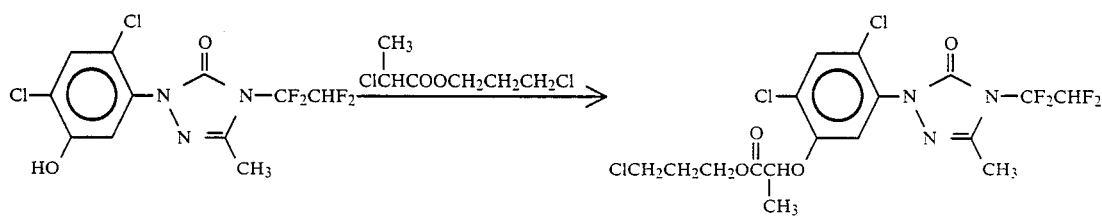

In 40 ml of anhydrous dimethylsulfoxide was dissolved 1.8 g (0.0051 mole) of 1-(2,4-dichloro-5-hydroxyphenyl)-3-methyl-4-(1,1,2,2-tetrafluoroethyl)-$\Delta^2$-1,2,4-triazolin-5-one, and 0.3 g (0.0053 mole) of powdered potassium hydroxide was added to the resulting solution. The mixture thus obtained was stirred for 30 minutes, after which 1.0 g (0.0053 mole) of 3-chloropropyl α-chloropropionate was added, and the reaction was carried out at 80° C. for 4 hours. After completion of the reaction, the reaction mixture was cooled to room temperature and poured into ice water, and the reaction product was extracted therefrom with diethyl ether. The extract was washed with water and dried. Then, the diethyl ether was removed by distillation to obtain 2.3 g of the desired compound: $n_D^{24}$ 1.5139, yield 89%.

EXAMPLE 4

1-{4-Chloro-5-[1-(3-chloropropoxycarbonyl)ethoxy]-2-fluorophenyl}-3-methyl-4-(1,1,2,2-tetrafluoroethyl)-$\Delta^2$-1,2,4-triazolin-5-one (Compound No. 32)

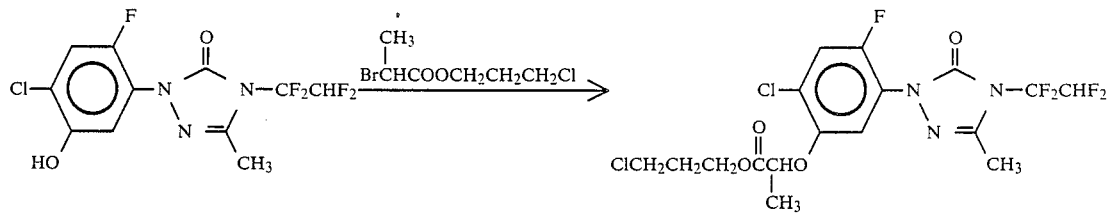

In 50 ml of N,N-dimethylformamide was suspended 0.52 g (0.0037 mole) of potassium carbonate, and 1.17 g (0.0034 mole) of 1-(4-chloro-2-fluoro-5-hydroxyphenyl)-3-methyl-4-(1,1,2,2-tetrafluoroethyl)-$\Delta^2$-1,2,4-triazolin-5-one was added to the resulting suspension. The resulting mixture was stirred at room temperature for 30 minutes, after which 0.85 g (0.0034 mole) of 3-chloroporpyl α-bromopropionate was added, and the reaction was carried out at 50° C. for 3 hours. After completion of the reaction, the reaction mixture was adjusted to room temperature and poured into ice water, and the reaction product was extracted therefrom with diethyl ether. The extract was washed with water and dried. Then, the diethyl ether was removed by distillation to obtain an oily substance. The oily substance obtained was purified by a silica gel column chromatography (ether : n-hexane=1:2) and allowed to stand at room temperature to obtain 1.36 g of the desired product as crystals: m.p. 48.5° C., yield 82%.

EXAMPLE 5

4-(2-Chloro-1,1,2-trifluoroethyl)-1-{2,4-dichloro-5-[1-((2-ethylthio)ethoxycarbonyl)ethoxy]phenyl}3-methyl-$\Delta^2$-1,2,4-triazolin-5-one (Compound No. 66)

In 30 ml of tetrahydrofuran was suspended 0.15 g (0.0037 mole) of 60% NaH, and 1.26 g (0.0034 mole) of 4-(2-chloro-1,1,2-trifluoroethyl)-1-(2,4-dichloro-5-hydroxyphenyl)-3-methyl-$\Delta^2$-1,2,4-triazolin-5-one was added to the resulting suspension. The mixture thus obtained was stirred for 30 minutes, after which 0.89 g (0.0037 mole) of (2-ethylthio)ethyl α-bromopropionate was added, and the resulting mixture was refluxed with heating for 5 hours. After completion of the reaction, the reaction mixture was cooled to room temperature and then poured into ice water, and the reaction product was extracted therefrom with diethyl ether. The extract was washed with water and dried. Then, the diethyl ether was removed by distillation, and the residue was purified by dry column chromatography to obtain 1.33 g of the desired compound: $n_D^{23}$ 1.5326, yield 75%.

EXAMPLE 6

1-{4-Chloro-5-[1-(4-chlorobenxzyloxycarbonyl)ethoxy]-2-fluorophenyl}-3-methyl-4-(1,1,2,2-tetrafluoroethyl)-$\Delta^2$-1,2,4-triazolin-5-one (Compound No. 87)

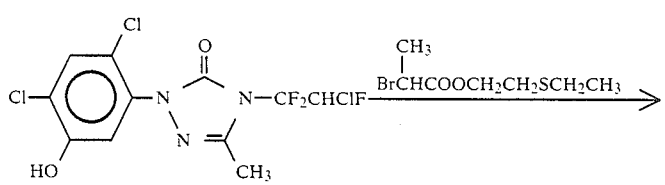

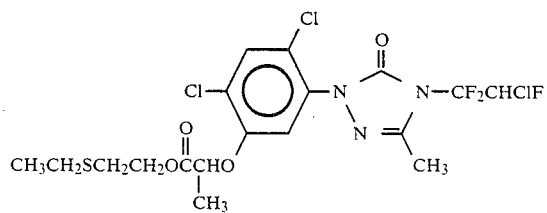

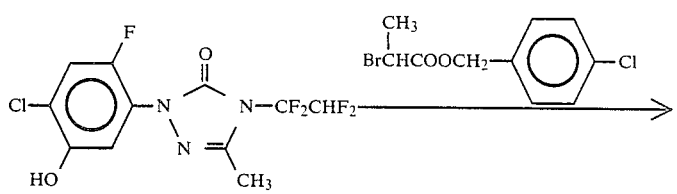

-continued

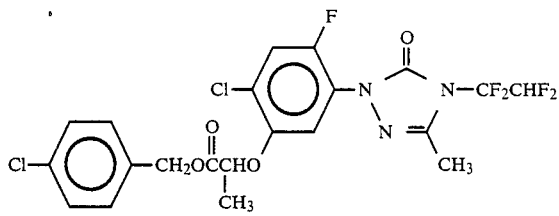

To 50 ml of methyl ethyl ketone were added 1.75 g (0.0051 mole) of 1-(4-chloro-1-fluoro-5-hydroxyphenyl)-3-methyl-4-(1,1,2,2,-tetrafluoroethyl)-$\Delta^2$-1,2,4-triazolin-5-one, 1.5 g of potassium carbonate and 1.27 g (5.6 m moles) of 4-chlorobenzyl α-bromopropionate, and the resulting mixture was refluxed with heating for 5 hours. After completion of the reaction, the reaction mixture was cooled to room temperature. Then, the insoluble materials were removed by filtration, and the filtrate was concentrated, after which the residue was purified by dry column chromatography to obtain 1.87 g of the desired compound: $n_D^{18}$ 1.5329, yield 68%.

EXAMPLE 7

Sodium 1-{2,4-dichloro-5-[3-methyl-4-(1,1,2,2-tetrafluoroethyl)-$\Delta^2$-1,2,4-triazolin-5-on-1-yl]phenoxy}propionate (Compound No. 6)

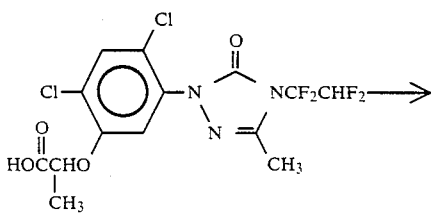

In 30 ml of methanol was dissolved 4.32 g (0.01 mole) of 1-{2,4-dichloro-5-[1-hydroxycarbonyl)ethyoxy]phenyl}-3-methyl-4-(1,1,2,2-tetrafluoroethyl)-$\Delta^2$1,2,4-triazolin-5-one, and 2 ml of an aqueous solution of 0.4 g (0.01 mole) of NaOH was added to the resulting solution. The solution thus obtained was stirred at room temperature for 30 minutes, after which the solvent was removed by distillation, and the crystals thus obtained were washed with ether and then dried to obtain 4.53 g of the desired compound: m.p. 141.8° C., yield 100%.

EXAMPLE 8

1-{2,4-Dichloro-5-[1-(2-methylsulfinyl)ethoxycarbonyl]ethyoxyphenyl}-3-methyl-4-(1,1,2,2-tetrafluoroethyl)-$\Delta^2$-1,2,4-triazolin-5-one (Compound No. 71)

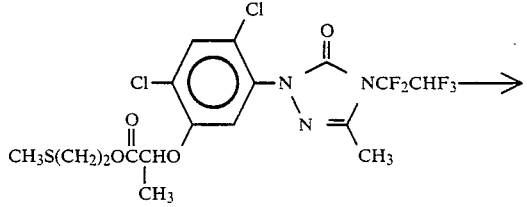

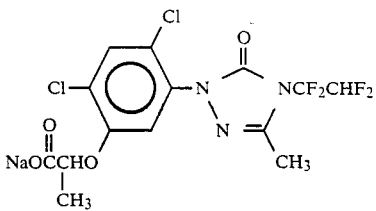

In 100 ml of methylene dichloride was dissolved 5.05 g (0.01 mole) of 1-{2,4-dichloro-5-[1-(2-methylthio)ethoxycarbonyl]ethoxyphenyl}-3-methyl-4-(1,1,2,2-tetrafluoroethyl)-$\Delta^2$-1,2,4-triazolin-5-one, and 2.0 g (0.0106 mole) of m-chloroperbenzoic acid was added. The resulting mixture was subjected to reaction at room temperature for 5 hours, after which the reaction mixture was poured into ice water, and the methylene chloride layer was treated by a conventional method to obtain 48 g of the desired compound: $n_D^{25}$ 1.5195, yield 92.1%.

The $\Delta^2$-1,2,4-triazolin-5-one derivatives represented by the general formula (I) of this invention are capable of controlling annual and perennial weeds grown in paddy fields, for example, barnyard grass (*Echinochloa crus-galli Beauv.*, an annual weed of Gramineae family which is a typical strongly injurious weed grown in paddy fields), monochoria (*Monochoria vaginalis Presl*, a strongly injurious annual weed of Pontederiaceae family grown in paddy fields), smallflower umbrellaplant (*Cyperus difformis L.*, and injurious annual weed of Cyperaceae family grown in paddy fields), water nutgrass Cyperus serotinus Rottb., a typical injurious perennial weed of Cyperaceae family grown in paddy fields, and also grown in swamps and waterways), arrowhead (*Sagittaria pygmaea Mig.*, an injurious perennial weed of Alismataceae family, grown in paddy fields, swamps and ditches), bulrush (*Scirpus juncoids Roxb.* var Hotarui Ohwi, a perennial weed of Cyperaceae family, grown in paddy fields, swamps and ditches); and annual and perennial weeds grown in upland fields and orchards, for example, wild oats (*Avena fatua L.*, an annual weed of Gramineae family, grown in plains, waste lands and upland fields), mugwort (*Artemisia princeps Pamp.*, a perennial weed of Compositae family, grown in cultivated and uncultivated fields), large crabgrass (*Digitaraia adscendcue Henr.*, an annual weed of Gramineae family which is a typical strongly injurious weed grown in upland fields and orchards), curly dock (*Rumex japonicus Houttuyn*, a perennial weed of Polygonaceae family, grown in upland fields and on roadsides), umbrella sedge (*Cyperus iria L.*, an annual weed of Cyperaceae family, grown in upland fields and on roadsides), redroot pigweed (*Amaranthus varidis L.*, an annual weed of Amaranthaceae family grown in upland fields, vacant lands and roadsides), and cocklebur (*Xanthium strumarium L.*, an annual weed of Compositae family, strongly injurious to soybeans).

Since, the triazolin-5-one derivatives represented by the above general formula (I) exhibit excellent controlling effects against weeds of both pre-and post-emergence stages, they are useful, for example, as herbicides for soil treatment before and after seeding (planting), for soil treatment in the growth period, for foliar treatment before seeding (planting), for foliar treatment in the growth period of useful upland crops such as soybeans, cotton, corns and the like. Furthermore, the compounds of this invention are useful as herbicides applying at the pre-emegence stage and the post-emergence stage of weeds in paddy fields, moreover, they are useful as herbicides to control general weeds grown in for example, mowed fields, paddy fields and upland fields in fallow, ridges between paddy fields, agricultural pathways, waterways, pasture, graveyards, parks, roads, playgrounds, unoccupied areas around buildings, reclaimed lands, railways and forests. Herbicidal treatments of such areas are carried out most effectively and economically when weeds are not emergent but not necessarily be done prior to the emergence of weeds.

For applying the compounds of the present invention as herbicides, they are generally formulated, according to conventional procedures for preparing agricultural compositions, into a form convenient to use.

That is to say, said compounds are mixed with suitable inert carriers and, if necessary, further mixed with adjuvants, in a suitable ratio, and through dissolution, dispersion, suspension, mechanical mixing, impregnation, adsorption or adhesion, to make to mixture into a suitable form of composition, e.g., suspensions, emulsifiable concentrates, solutions, wettable powders, dusts, granules or tablets.

The inert carriers usable in this invention may be either solid or liquid. As materials usable as the solid carriers, there can be examplified, for example, vegetable powders such as soybean flour, cereal flour, wood flour, bark flour, saw dust, powdered tobaco stalks, powdered walnut shell, bran, powdered cellulose, and extraction residues of vegetables; fibrous materials such as paper, corrugated paperboard, and waste cloths; synthetic polymers such as powdered synthetic resins; inorganic or mineral products such as clays (e.g., kaolin, bentonite and acid clay), talc products (e.g., talc and pyrophyllite), silica products [e.g., diatomaceous earth, silica sand, mica and white carbon (a highly dispersed synthetic silicic acid, also called as finely pulverized hydrated silica or hydrated silicic acid, and some commercially available products contain calcium silicate as the major component)], activated carbon, powdered sulfur, pumice, calcined diatomaceous earth, ground brick, fly ash, sand, calcium carbonate, and calcium phosphates; chemical fertilizers such as ammonium sulfate, ammonium phosphates, ammonium nitrate, urea, and ammonium chloride, and farmyard manures. These solid carriers may be used alone or as a mixture thereof. Materials usable as the liquid carriers are selected from those which are solvents for the active ingredients and those which are non-solvnet but can disperse the active ingredients with the aid of adjuvants. They include, for example, the following materials, which may be used alone or as a mixture thereof: water, alcohols (e.g., methanol, ethanol, isopropanol, butanol, and ethylene glycol), ketones (e.g., acetone, methyl ethyl ketone, methyl isobutyl ketone, diisobutyl ketone, and cyclohexanone), ethers (e.g., ethyl ether, dioxane, cellosolves, dipropyl ether, and tetrahydrofuran), aliphatic hydrocarbons (e.g., gasoline and mineral oils), aromatic hydrocarbons (e.g., benzene, toluene, xylene, solvent naphtha, and alkylnaphthalene), halogenated hydrocarbones (e.g., dichloroethane, chlorinated benzenes, chloroform and carbon tetrachloride), esters (e.g., ethyl acetate, dibutyl phthalate, diisopropyl phthanate, and dioctyl phthalate), acid amides (e.g., dimethylformamide, diethylformamide, and dimethylacetamide), and nitriles (e.g., acetonitrile), and dimethyl sulfoxide.

As the adjuvants, the following can be examplified. These adjuvants are used depending on purposes. In some cases, two or more of the adjuvants are simultaneously used. In some other cases, no adjuvant is used at all. For the purpose of emulsification, dispersion, solubilization and/or wetting of the active ingredients, there can be used furface active agents, for example, polyoxyethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates, and higher alcohol sulfate esters. For the purpose of stabilizing the dispersion, tackification and/or agglomeration of the active ingredients, the following materials may be use, for example, casein, gelatin, starch, alginic acid, methylcellulose, carboxymethylcellulose, gum arabic, polyvinyl alcohol, pine root oil, rice bran oil, bentonite and ligninsulfonates.

For the purpose of improving the flowability of the solid compositions, it is recommendable to use waxes, stearates, alkyl phosphates, etc.

As to peptizers for dispersible compositions, it is also recommendable to use naphthalenesulfonic acid condensation products, condensed phosphates, etc.

It is also possible to add anti-foaming agents, for example, a silicone oil.

The content of the active ingredients in the herbicidal composition may be adjusted depending on the applications. In general, it is suitably 0.5 to 20% by weight for preparing a powdered or granulated product, and 0.1 to 50% by weight for preparing an emulsifiable concentrate or a wettable powder product.

For destroying various weeds, inhibiting their growth, or protecting useful plants from the injury caused by these weeds, the herbicidal composition of the present invention is applied in a weed-destroying dosage or a weed growth inhibiting dosage as such or after being properly diluted with or suspended in water or in other suitable medium, to the soil or the foliage of weeds in the area where the emergence or growth of weeds is undesirable.

The amount of the herbicidal composition of the present invention used is varied depending on various factors, for example, the purpose of application, the objective weeds, the emergence or growth state of weeds and crops, the emergence tendency of weeds, weather, environmental conditions, the type of herbicidal formulations, the way of application, the type of the field to be treated, and the time of application and others.

When the herbicidal composition of this invention is applied alone as a selective herbicide, it is suitable, for example, to select the dosage of the compound of this invention in the range of 0.1 to 500 g per 10 ares. On the other hand, when the herbicidal composition of this invention is applied together with other herbicides, the dosage of the compound of this invention can be selected in a still smaller dosage range when it is taken into consideration that said composition is often effective in a smaller dosage than when it is used alone.

Herbicidal composition of the present invention is especially valuable for the pre-emergence treatment and initial emergence stage treatment of upland fields and for the control of weeds at pre-emergence stage and post-emergence stage in paddy fields. In order to expand both spectrum of controllable weed species and the period of time when effective applications are possible or to reduce the dosage, the herbicidal composition of the present invention can be used in combination with other herbicides, and this usage is within the scope of the present invention. For example, herbicidal composition of the present invention can be used in combination with one or more of the following herbicides: phenoxy fatty acid type herbicides, for example, 2,4-PA (e.g., ethyl (2,4-dichlorophenoxy)acetate), MCP (e.g., ethyl (2-methyl-4-chlorophenoxy)acetate, sodium (2-methyl-4-chlorophenoxy)acetate, and allyl (2-methyl-4-chlorophenoxy)acetate), MCPB (ethyl (2-methyl-4-chlorophenoxy)butyrate), and Diclofop-methyl (methyl 2-[4-(2,4-dichlorophenoxy)phenoxy]propanoate); diphenyl ether type herbicides, for example, NIP (2,4-dichlorophenyl-4'-nitrophenyl ether), CNP (2,4,6-trichlorophenyl-4'-nitrophenyl ether), Chlomethoxynil (2,4-dichlorophenyl-3'-methoxy-4'-nitrophenyl ether), Acifluorgen [5-(2-chloro-α,α,α-trifluoro-p-tolyloxy)-2-nitrobenzoic acid and its salts], and Fluazifop-butyl (butyl (±)-2-[4-[[5-(trifluoromethyl)-2-pyridyl]oxy]phenoxy]propionate); triazine type herbicides, for example, CAT (2-chloro-4,6-bis(ethylamino)-s-triazine), Prometryne (2-methylthio-4,6-bis(isopropylamino)-s-triazine, Simetryne (2-methylthio-4,6-bis(ethylamino)-s-triazine), and Metribuzin (4-amino-6-tert-butyl-3-methylthio-1,2,4-tirazin-5(4H)-one); carbamate type herbicides, for example, Molinate (s-ethyl hexahydro-1H-azepine-1-carbothioate), MCC (methyl N-(3,4-dichlorophenyl)carbamate), IPC (isopropyl N-(3-chlorophenyl)carbamate), and Benthiocarb (s-(4-chlorobenzyl)dimethylthiocarbamate); toluidine type herbicides, for example, Triefluraline (α,α, α-trifluoro-2,6-dinitro-N,N-dipropyl-p-toluidine) and Pendimethaline (N-(1-ethylpropyl)-2,6-dinitro-3,4-xylidine); Acid amide type herbicides, for example, DCPA (3,4-dichloropropionanilide), Butachlor (2-chloro-2',6'-diethyl-N-(butoxymethyl)-acetanilide), Alachlor (2-chloro-2',6'-diethyl-N-(methoxyethyl)acetanilide), Metolachlor (2-chloro-N-(2-ethyl-6-methylphenyl)-N-(2-methoxy-1-methylethyl)acetamide), and Pretilachlor (2-chloro-2',6'-diethyl-N-(2-propoxyethyl)acetanilide); and other types of herbicides, for example, DCMU (3-(3,4-dichlorophenyl)-1,1-dimethylurea), Bentazon (3-isopropyl-(1H)-2,1,3-benzothiazin-4(3H)-one-2,2-dioxide), Pyrazolate (4-(2,4-dichlorobenzoyl)-1,3-dimethylpyrazol-5-yl-p-toluenesulfonate), Pyrazoxyfen (1,3-dimethyl-4-(2,4-dichlorobenzoyl)-5-phenacyloxypyrazol), and MY-71 (4-(2,4-dichloro-3-methylbenzoyl)-1,3-dimethylpyrazol-5-yl-p-toluenesulfonate).

Some test examples and preparation examples are given below not by way of limitation but by way of illustration.

Test Example 1

Effect on paddy field weeds of pre-emergence stage

Pots (1/10,000 - are)) were filled with soil to simulate a paddy field, and planted with seeds of barnyard grass, monochoria, umbrella plant, and bulrush, and with tubers of arrowhead, respectively, which are all injurious weeds grown in paddy, fields, and the seeds and tubers were conditioned so as to be in preemergence stage.

The soil in the pot was treated with each of the active ingredients (the compounds listed in Table 1) formulated to given concentration of liquid, by spraying. After 21 days, the percent control of weed growth compared with that on the untreated plot was observed and the herbicidal activity was determined according to the following criterion:

Criterion for determining herbicidal activity

| Degree of herbicidal activity | Percent control of weed growth (%) |
|---|---|
| 5 | 100 |
| 4 | 90–99 |
| 3 | 80–89 |
| 2 | 70–79 |
| 1 | Less than 70 |

The results obtained are shown in Table 2.

TABLE 2

| Compound No. | Amount of active ingredient g/are | Effect of pre-emergence treatment | | | | |
| | | Barnyard grass | Monochoria | Umbrella plant | Bulrush | Arrowhead |
|---|---|---|---|---|---|---|
| 1 | 30 | 5 | 5 | 5 | 5 | 5 |
|   | 3  | 4 | 5 | 5 | 5 | 5 |
| 2 | 30 | 5 | 5 | 5 | 5 | 5 |
|   | 3  | 4 | 5 | 5 | 5 | 5 |
| 3 | 30 | 5 | 5 | 5 | 5 | 5 |
|   | 3  | 5 | 5 | 5 | 5 | 5 |
| 4 | 30 | 5 | 5 | 5 | 5 | 5 |
|   | 3  | 5 | 5 | 5 | 5 | 5 |
| 5 | 30 | 5 | 5 | 5 | 5 | 5 |
|   | 3  | 5 | 5 | 5 | 5 | 5 |
| 6 | 30 | 5 | 5 | 5 | 5 | 5 |
|   | 3  | 5 | 5 | 5 | 5 | 5 |
| 7 | 30 | 5 | 5 | 5 | 5 | 5 |
|   | 3  | 5 | 5 | 5 | 5 | 5 |

TABLE 2-continued

| Compound No. | Amount of active ingredient g/are | Barnyard grass | Effect of pre-emergence treatment | | | |
|---|---|---|---|---|---|---|
| | | | Monochoria | Umbrella plant | Bulrush | Arrowhead |
| 8 | 30 | 5 | 5 | 5 | 5 | 5 |
| | 3 | 5 | 5 | 5 | 5 | 5 |
| 9 | 30 | 5 | 5 | 5 | 5 | 5 |
| | 3 | 5 | 5 | 5 | 5 | 5 |
| 10 | 30 | 5 | 5 | 5 | 5 | 5 |
| | 3 | 4 | 5 | 5 | 4 | 4 |
| 11 | 30 | 5 | 5 | 5 | 5 | 5 |
| | 3 | 5 | 5 | 5 | 5 | 5 |
| 12 | 30 | 5 | 5 | 5 | 5 | 5 |
| | 3 | 5 | 5 | 5 | 4 | 5 |
| 13 | 30 | 5 | 5 | 5 | 5 | 5 |
| | 3 | 5 | 5 | 5 | 5 | 5 |
| 14 | 30 | 5 | 5 | 5 | 5 | 5 |
| | 3 | 5 | 5 | 5 | 5 | 5 |
| 15 | 30 | 5 | 5 | 5 | 5 | 5 |
| | 3 | 5 | 5 | 5 | 5 | 5 |
| 16 | 30 | 5 | 5 | 5 | 5 | 5 |
| | 3 | 5 | 5 | 5 | 5 | 5 |
| 17 | 30 | 5 | 5 | 5 | 5 | 5 |
| | 3 | 5 | 5 | 5 | 5 | 5 |
| 18 | 30 | 5 | 5 | 5 | 5 | 5 |
| | 3 | 5 | 5 | 5 | 5 | 5 |
| 19 | 30 | 5 | 5 | 5 | 5 | 5 |
| | 3 | 5 | 5 | 5 | 5 | 5 |
| 20 | 30 | 5 | 5 | 5 | 5 | 5 |
| | 3 | 5 | 5 | 5 | 5 | 5 |
| 21 | 30 | 5 | 5 | 5 | 5 | 5 |
| | 3 | 5 | 5 | 5 | 5 | 5 |
| 22 | 30 | 5 | 5 | 5 | 5 | 5 |
| | 3 | 5 | 5 | 5 | 5 | 5 |
| 23 | 30 | 5 | 5 | 5 | 5 | 5 |
| | 3 | 5 | 5 | 5 | 5 | 5 |
| 24 | 30 | 5 | 5 | 5 | 5 | 5 |
| | 3 | 5 | 5 | 5 | 5 | 5 |
| 25 | 30 | 5 | 5 | 5 | 5 | 5 |
| | 3 | 5 | 5 | 5 | 5 | 5 |
| 26 | 30 | 5 | 5 | 5 | 5 | 5 |
| | 3 | 5 | 5 | 5 | 5 | 5 |
| 27 | 30 | 5 | 5 | 5 | 5 | 5 |
| | 3 | 5 | 5 | 5 | 5 | 5 |
| 28 | 30 | 5 | 5 | 5 | 5 | 5 |
| | 3 | 5 | 5 | 5 | 5 | 5 |
| 29 | 30 | 5 | 5 | 5 | 5 | 5 |
| | 3 | 5 | 5 | 5 | 5 | 5 |
| 30 | 30 | 5 | 5 | 5 | 5 | 5 |
| | 3 | 5 | 5 | 5 | 5 | 5 |
| 31 | 30 | 5 | 5 | 5 | 5 | 5 |
| | 3 | 4 | 5 | 5 | 5 | 5 |
| 32 | 30 | 5 | 5 | 5 | 5 | 5 |
| | 3 | 5 | 5 | 5 | 5 | 5 |
| 33 | 30 | 5 | 5 | 5 | 5 | 5 |
| | 3 | 5 | 5 | 5 | 5 | 5 |
| 34 | 30 | 5 | 5 | 5 | 5 | 5 |
| | 3 | 5 | 5 | 5 | 5 | 5 |
| 35 | 30 | 5 | 5 | 5 | 5 | 5 |
| | 3 | 5 | 5 | 5 | 5 | 5 |
| 36 | 30 | 5 | 5 | 5 | 5 | 5 |
| | 3 | 5 | 5 | 5 | 5 | 5 |
| 37 | 30 | 5 | 5 | 5 | 5 | 5 |
| | 3 | 5 | 5 | 5 | 5 | 5 |
| 38 | 30 | 5 | 5 | 5 | 5 | 5 |
| | 3 | 5 | 5 | 5 | 5 | 5 |
| 39 | 30 | 5 | 5 | 5 | 5 | 5 |
| | 3 | 5 | 5 | 5 | 5 | 5 |
| 40 | 30 | 5 | 5 | 5 | 5 | 5 |
| | 3 | 5 | 5 | 5 | 5 | 5 |
| 41 | 30 | 5 | 5 | 5 | 5 | 5 |
| | 3 | 5 | 5 | 5 | 5 | 5 |
| 42 | 30 | 5 | 5 | 5 | 5 | 5 |
| | 3 | 5 | 5 | 5 | 5 | 5 |
| 43 | 30 | 5 | 5 | 5 | 5 | 5 |
| | 3 | 5 | 5 | 5 | 5 | 5 |
| 44 | 30 | 5 | 5 | 5 | 5 | 5 |
| | 3 | 5 | 5 | 5 | 5 | 5 |
| 45 | 30 | 5 | 5 | 5 | 5 | 5 |
| | 3 | 5 | 5 | 5 | 5 | 5 |
| 46 | 30 | 5 | 5 | 5 | 5 | 5 |
| | 3 | 5 | 5 | 5 | 5 | 5 |

TABLE 2-continued

| Compound No. | Amount of active ingredient g/are | Effect of pre-emergence treatment | | | | |
|---|---|---|---|---|---|---|
| | | Barnyard grass | Monochoria | Umbrella plant | Bulrush | Arrowhead |
| 47 | 30 | 5 | 5 | 5 | 5 | 5 |
| | 3 | 5 | 5 | 5 | 4 | 5 |
| 48 | 30 | 5 | 5 | 5 | 5 | 5 |
| | 3 | 5 | 5 | 5 | 5 | 5 |
| 49 | 30 | 5 | 5 | 5 | 5 | 5 |
| | 3 | 5 | 5 | 5 | 4 | 5 |
| 50 | 30 | 5 | 5 | 5 | 5 | 5 |
| | 3 | 5 | 5 | 5 | 5 | 5 |
| 51 | 30 | 5 | 5 | 5 | 5 | 5 |
| | 3 | 5 | 5 | 5 | 5 | 5 |
| 52 | 30 | 5 | 5 | 5 | 5 | 5 |
| | 3 | 5 | 5 | 5 | 5 | 5 |
| 53 | 30 | 5 | 5 | 5 | 5 | 5 |
| | 3 | 4 | 5 | 5 | 5 | 5 |
| 54 | 3- | 5 | 5 | 5 | 5 | 5 |
| | 3 | 5 | 5 | 5 | 5 | 5 |
| 55 | 30 | 5 | 5 | 5 | 5 | 5 |
| | 3 | 5 | 5 | 5 | 5 | 5 |
| 56 | 30 | 5 | 5 | 5 | 5 | 5 |
| | 3 | 5 | 5 | 5 | 5 | 5 |
| 57 | 30 | 5 | 5 | 5 | 5 | 5 |
| | 3 | 5 | 5 | 5 | 5 | 5 |
| 58 | 30 | 5 | 5 | 5 | 5 | 5 |
| | 3 | 5 | 5 | 5 | 5 | 5 |
| 59 | 30 | 5 | 5 | 5 | 5 | 5 |
| | 3 | 5 | 5 | 5 | 5 | 5 |
| 60 | 30 | 5 | 5 | 5 | 5 | 5 |
| | 3 | 5 | 5 | 5 | 5 | 5 |
| 61 | 30 | 5 | 5 | 5 | 5 | 5 |
| | 3 | 5 | 5 | 5 | 5 | 5 |
| 62 | 30 | 5 | 5 | 5 | 5 | 5 |
| | 3 | 5 | 5 | 5 | 5 | 5 |
| 63 | 30 | 5 | 5 | 5 | 5 | 5 |
| | 3 | 4 | 5 | 4 | 4 | 5 |
| 64 | 30 | 5 | 5 | 5 | 5 | 5 |
| | 3 | 5 | 5 | 5 | 5 | 5 |
| 65 | 30 | 5 | 5 | 5 | 5 | 5 |
| | 3 | 4 | 5 | 4 | 4 | 5 |
| 66 | 30 | 5 | 5 | 5 | 5 | 5 |
| | 3 | 5 | 5 | 5 | 5 | 5 |
| 67 | 30 | 5 | 5 | 5 | 5 | 5 |
| | 3 | 4 | 4 | 4 | 4 | 5 |
| 68 | 30 | 5 | 5 | 5 | 5 | 5 |
| | 3 | 5 | 5 | 5 | 5 | 5 |
| 69 | 30 | 5 | 5 | 5 | 5 | 5 |
| | 3 | 5 | 5 | 5 | 5 | 5 |
| 70 | 30 | 5 | 5 | 5 | 5 | 5 |
| | 3 | 5 | 5 | 5 | 5 | 5 |
| 71 | 30 | 5 | 5 | 5 | 5 | 5 |
| | 3 | 5 | 5 | 5 | 5 | 5 |
| 72 | 30 | 5 | 5 | 5 | 5 | 5 |
| | 3 | 5 | 5 | 5 | 5 | 5 |
| 73 | 30 | 5 | 5 | 5 | 5 | 5 |
| | 3 | 5 | 5 | 5 | 5 | 5 |
| 74 | 30 | 5 | 5 | 5 | 5 | 5 |
| | 3 | 5 | 5 | 5 | 5 | 5 |
| 75 | 30 | 5 | 5 | 5 | 5 | 5 |
| | 3 | 5 | 5 | 5 | 5 | 5 |
| 76 | 30 | 5 | 5 | 5 | 5 | 5 |
| | 3 | 4 | 5 | 5 | 5 | 5 |
| 77 | 30 | 5 | 5 | 5 | 5 | 5 |
| | 3 | 5 | 5 | 5 | 5 | 5 |
| 78 | 30 | 5 | 5 | 5 | 5 | 5 |
| | 3 | 5 | 5 | 5 | 5 | 5 |
| 79 | 30 | 5 | 5 | 5 | 5 | 5 |
| | 3 | 5 | 5 | 5 | 5 | 5 |
| 80 | 30 | 5 | 5 | 5 | 5 | 5 |
| | 3 | 5 | 5 | 5 | 5 | 5 |
| 81 | 30 | 5 | 5 | 5 | 5 | 5 |
| | 3 | 5 | 5 | 5 | 5 | 5 |
| 82 | 30 | 5 | 5 | 5 | 5 | 5 |
| | 3 | 5 | 5 | 5 | 5 | 5 |
| 83 | 30 | 5 | 5 | 5 | 5 | 5 |
| | 3 | 5 | 5 | 5 | 5 | 5 |
| 84 | 30 | 5 | 5 | 5 | 5 | 5 |
| | 3 | 5 | 5 | 5 | 5 | 5 |
| 85 | 30 | 5 | 5 | 5 | 5 | 5 |
| | 3 | 5 | 5 | 5 | 5 | 5 |

TABLE 2-continued

| Compound No. | Amount of active ingredient g/are | Effect of pre-emergence treatment | | | | |
|---|---|---|---|---|---|---|
| | | Barnyard grass | Monochoria | Umbrella plant | Bulrush | Arrowhead |
| 86 | 30 | 5 | 5 | 5 | 5 | 5 |
| | 3 | 5 | 5 | 5 | 5 | 5 |
| 87 | 30 | 5 | 5 | 5 | 5 | 5 |
| | 3 | 5 | 5 | 5 | 5 | 5 |
| 88 | 30 | 5 | 5 | 5 | 5 | 5 |
| | 3 | 5 | 5 | 5 | 5 | 5 |
| 89 | 30 | 5 | 5 | 5 | 5 | 5 |
| | 3 | 5 | 5 | 5 | 5 | 5 |
| 90 | 30 | 5 | 5 | 5 | 5 | 5 |
| | 3 | 5 | 5 | 5 | 5 | 5 |
| 91 | 30 | 5 | 5 | 5 | 5 | 5 |
| | 3 | 5 | 5 | 5 | 5 | 5 |
| Compound A | 30 | 5 | 5 | 5 | 5 | 5 |
| | 3 | 3 | 4 | 4 | 3 | 3 |
| Compound B | 30 | 4 | 5 | 5 | 4 | 5 |
| | 3 | 1 | 4 | 5 | 1 | 3 |
| Compound C | 3 | 3 | 4 | 4 | 3 | 3 |

As reference Compound A, Compound 7 (1-(2,4-dichloro-5-((1-ethoxycarbonyl)-ethoxy)phenyl)-4-difluoromethyl-3-methyl-Δ²-1,2,4-triazolin-5-one) disclosed in Japanese Patent Kokai No. 57-181069 (1982) was tested, respectively.
*¹Compound B, Compound No. 62 1-[2,4-dichloro-5-(1-ethoxycarbonyl)ethoxyphenyl]-4-ethyl-3-methyl-Δ²1,2,4-triazolin-5-one disclosed in U.S. Pat. No. 4318731
*²Compound C, Compound No. 5 1-(2,4-dichloro-5-isopropoxyphenyl)-4-difluoromethyl-3-methyl-Δ²-1,2,4-triazolin-5-one disclosed in U.S. Pat. No. 4398943

Test Example 2

Effect on paddy field weeds of post-emergence stage

Pots (1/10,000 - are) were filled with soil to simulate a paddy field and grown with each of injurious weeds of the following leaf age. In addition, young seedings of rice plant (cultivar: "Nihonbare") of the 2.5 leaf age were transplanted to the soil on the day before the treatment with each of the present herbicides, and treated with the herbicides. After 21 days, the herbicidal effect and the degree of crop injury to the rice plant were evaluated by comparing the results with those on the untreated plot.

| Species of weed tested | Leaf age of the weed |
|---|---|
| Barnyard grass | 1 |
| Monochoria | 2-3 |
| Umbrella plant | 1-2 |
| Bulrush | 2-3 |
| Arrowhead | 3 |
| Water nutgrass | 1-2 |

The criterion for judging the degree of crop injury was as follows:
H: High (including withering)
M: Medium
L: Low
N: None The criterion for judging the herbicidal activity was the same as in Test Example 1. The results obtained are shown in Table 3.

TABLE 3

| Compound No. | Amount of active ingredient g/are | Effect of Post-emergence treatment | | | | | | Crop injury Rice |
|---|---|---|---|---|---|---|---|---|
| | | Barnyard grass | Monochoria | Umbrella plant | Bulrush | Arrowhead | Water nutgrass | |
| 1 | 30 | 5 | 5 | 5 | 5 | 5 | 5 | L |
| | 3 | 3 | 5 | 5 | 4 | 4 | 4 | N |
| 2 | 30 | 5 | 5 | 5 | 5 | 5 | 5 | L |
| | 3 | 4 | 5 | 5 | 4 | 4 | 5 | N |
| 3 | 30 | 5 | 5 | 5 | 5 | 5 | 5 | L |
| | 3 | 5 | 5 | 5 | 5 | 5 | 5 | L |
| 4 | 30 | 5 | 5 | 5 | 5 | 5 | 5 | L |
| | 3 | 4 | 5 | 5 | 5 | 5 | 5 | N |
| 5 | 30 | 5 | 5 | 5 | 5 | 5 | 5 | L |
| | 3 | 5 | 5 | 5 | 5 | 5 | 5 | L |
| 6 | 30 | 5 | 5 | 5 | 5 | 5 | 5 | L |
| | 3 | 4 | 5 | 5 | 4 | 5 | 5 | N |
| 7 | 30 | 5 | 5 | 5 | 5 | 5 | 5 | L |
| | 3 | 5 | 5 | 5 | 5 | 5 | 5 | L |
| 8 | 30 | 5 | 5 | 5 | 5 | 5 | 5 | L |
| | 3 | 5 | 5 | 5 | 5 | 5 | 5 | L |
| 9 | 30 | 5 | 5 | 5 | 5 | 5 | 5 | L |
| | 3 | 4 | 5 | 5 | 4 | 5 | 5 | N |
| 10 | 30 | 5 | 5 | 5 | 5 | 5 | 5 | L |
| | 3 | 4 | 5 | 5 | 4 | 4 | 5 | N |
| 11 | 30 | 5 | 5 | 5 | 5 | 5 | 5 | L |
| | 3 | 4 | 5 | 5 | 5 | 5 | 5 | N |
| 12 | 30 | 5 | 5 | 5 | 5 | 5 | 5 | L |
| | 3 | 5 | 5 | 5 | 4 | 4 | 4 | N |
| 13 | 30 | 5 | 5 | 5 | 5 | 5 | 5 | L |

TABLE 3-continued

| Compound No. | Amount of active ingredient g/are | Effect of Post-emergence treatment | | | | | | Crop injury Rice |
|---|---|---|---|---|---|---|---|---|
| | | Barnyard grass | Mono-choria | Umbrella plant | Bulrush | Arrow-head | Water nutgrass | |
| 14 | 3 | 4 | 5 | 5 | 5 | 5 | 5 | L |
|    | 30 | 5 | 5 | 5 | 5 | 5 | 5 | L |
| 15 | 3 | 5 | 5 | 5 | 4 | 5 | 5 | L |
|    | 30 | 5 | 5 | 5 | 5 | 5 | 5 | L |
| 16 | 3 | 5 | 5 | 5 | 5 | 5 | 5 | L |
|    | 30 | 5 | 5 | 5 | 5 | 5 | 5 | L |
| 17 | 3 | 5 | 5 | 5 | 4 | 5 | 5 | L |
|    | 30 | 5 | 5 | 5 | 5 | 5 | 5 | L |
| 18 | 3 | 4 | 5 | 5 | 5 | 5 | 5 | L |
|    | 30 | 5 | 5 | 5 | 5 | 5 | 5 | L |
| 19 | 3 | 5 | 5 | 5 | 5 | 5 | 5 | L |
|    | 30 | 5 | 5 | 5 | 5 | 5 | 5 | L |
| 20 | 3 | 5 | 5 | 5 | 5 | 5 | 5 | L |
|    | 30 | 5 | 5 | 5 | 5 | 5 | 5 | L |
| 21 | 3 | 5 | 5 | 5 | 5 | 5 | 5 | L |
|    | 30 | 5 | 5 | 5 | 5 | 5 | 5 | L |
| 22 | 3 | 5 | 5 | 5 | 5 | 5 | 5 | L |
|    | 30 | 5 | 5 | 5 | 5 | 5 | 5 | L |
| 23 | 3 | 5 | 5 | 5 | 5 | 5 | 5 | L |
|    | 30 | 5 | 5 | 5 | 5 | 5 | 5 | L |
| 24 | 3 | 5 | 5 | 5 | 5 | 5 | 5 | L |
|    | 30 | 5 | 5 | 5 | 5 | 5 | 5 | L |
| 25 | 3 | 5 | 5 | 5 | 5 | 5 | 5 | L |
|    | 30 | 4 | 5 | 5 | 5 | 5 | 5 | L |
| 26 | 3 | 5 | 5 | 5 | 5 | 5 | 5 | L |
|    | 30 | 4 | 5 | 5 | 4 | 5 | 5 | L |
| 27 | 3 | 5 | 5 | 5 | 5 | 5 | 5 | L |
|    | 30 | 5 | 5 | 5 | 5 | 5 | 5 | N |
| 28 | 3 | 5 | 5 | 5 | 5 | 5 | 5 | L |
|    | 30 | 4 | 5 | 5 | 5 | 4 | 5 | L |
| 29 | 3 | 5 | 5 | 5 | 5 | 5 | 5 | L |
|    | 30 | 5 | 5 | 5 | 4 | 5 | 4 | N |
| 30 | 3 | 5 | 5 | 5 | 5 | 5 | 5 | L |
|    | 30 | 5 | 5 | 5 | 5 | 5 | 5 | L |
| 31 | 3 | 5 | 5 | 5 | 5 | 5 | 5 | L |
|    | 30 | 3 | 5 | 5 | 4 | 5 | 5 | L |
| 32 | 3 | 5 | 5 | 5 | 5 | 5 | 5 | L |
|    | 30 | 5 | 5 | 5 | 5 | 5 | 5 | L |
| 33 | 3 | 5 | 5 | 5 | 5 | 5 | 5 | L |
|    | 30 | 5 | 5 | 5 | 5 | 5 | 5 | L |
| 34 | 3 | 5 | 5 | 5 | 5 | 5 | 5 | L |
|    | 30 | 5 | 5 | 5 | 5 | 5 | 5 | L |
| 35 | 3 | 4 | 5 | 5 | 5 | 4 | 5 | L |
|    | 30 | 5 | 5 | 5 | 5 | 5 | 5 | L |
| 36 | 3 | 4 | 5 | 5 | 5 | 5 | 5 | L |
|    | 30 | 5 | 5 | 5 | 5 | 5 | 5 | L |
| 37 | 3 | 5 | 5 | 5 | 5 | 5 | 5 | L |
|    | 30 | 5 | 5 | 5 | 5 | 5 | 5 | L |
| 38 | 3 | 4 | 5 | 5 | 4 | 4 | 5 | L |
|    | 30 | 5 | 5 | 5 | 5 | 5 | 5 | L |
| 39 | 3 | 5 | 5 | 5 | 5 | 5 | 5 | L |
|    | 30 | 5 | 5 | 5 | 5 | 5 | 5 | Rice |
| 40 | 3 | 4 | 5 | 5 | 4 | 5 | 5 | L |
|    | 30 | 5 | 5 | 5 | 5 | 5 | 5 | L |
| 41 | 3 | 5 | 5 | 5 | 4 | 5 | 5 | L |
|    | 30 | 5 | 5 | 5 | 5 | 5 | 5 | L |
| 42 | 3 | 5 | 5 | 5 | 5 | 5 | 5 | L |
|    | 30 | 5 | 5 | 5 | 5 | 5 | 5 | L |
| 43 | 3 | 5 | 5 | 5 | 4 | 5 | 5 | L |
|    | 30 | 5 | 5 | 5 | 5 | 5 | 5 | L |
| 44 | 3 | 4 | 5 | 5 | 4 | 5 | 5 | N |
|    | 30 | 5 | 5 | 5 | 5 | 5 | 5 | L |
| 45 | 3 | 5 | 5 | 5 | 5 | 5 | 5 | L |
|    | 30 | 5 | 5 | 5 | 5 | 5 | 5 | L |
| 46 | 3 | 4 | 5 | 5 | 5 | 5 | 5 | L |
|    | 30 | 4 | 5 | 5 | 5 | 5 | 5 | L |
| 47 | 3 | 4 | 5 | 5 | 4 | 4 | 5 | N |
|    | 30 | 5 | 5 | 5 | 5 | 5 | 5 | L |
| 48 | 3 | 4 | 5 | 5 | 4 | 5 | 5 | L |
|    | 30 | 5 | 5 | 5 | 5 | 5 | 5 | L |
| 49 | 3 | 5 | 5 | 5 | 4 | 5 | 5 | L |
|    | 30 | 5 | 5 | 5 | 5 | 5 | 5 | L |
| 50 | 3 | 5 | 5 | 5 | 4 | 5 | 5 | N |
|    | 30 | 5 | 5 | 5 | 5 | 5 | 5 | L |
| 51 | 3 | 5 | 5 | 5 | 5 | 5 | 5 | L |
|    | 30 | 5 | 5 | 5 | 5 | 5 | 5 | L |
| 52 | | | | | | | | |

TABLE 3-continued

| Compound No. | Amount of active ingredient g/are | Barnyard grass | Mono-choria | Umbrella plant | Bulrush | Arrow-head | Water nutgrass | Crop injury Rice |
|---|---|---|---|---|---|---|---|---|
|  | 3 | 5 | 5 | 5 | 5 | 5 | 5 | L |
| 53 | 30 | 5 | 5 | 5 | 5 | 5 | 5 | L |
|  | 3 | 4 | 5 | 5 | 5 | 5 | 5 | L |
| 54 | 30 | 5 | 5 | 5 | 5 | 5 | 5 | L |
|  | 3 | 5 | 5 | 5 | 5 | 5 | 5 | L |
| 55 | 30 | 5 | 5 | 5 | 5 | 5 | 5 | L |
|  | 3 | 5 | 5 | 5 | 5 | 5 | 5 | L |
| 56 | 30 | 5 | 5 | 5 | 5 | 5 | 5 | L |
|  | 3 | 4 | 5 | 5 | 4 | 5 | 5 | N |
| 57 | 30 | 5 | 5 | 5 | 5 | 5 | 5 | L |
|  | 3 | 5 | 5 | 5 | 5 | 5 | 5 | L |
| 58 | 30 | 5 | 5 | 5 | 5 | 5 | 5 | L |
|  | 3 | 5 | 5 | 5 | 5 | 5 | 5 | L |
| 59 | 30 | 5 | 5 | 5 | 5 | 5 | 5 | L |
|  | 3 | 5 | 5 | 5 | 5 | 5 | 5 | L |
| 60 | 30 | 5 | 5 | 5 | 5 | 5 | 5 | L |
|  | 3 | 5 | 5 | 5 | 5 | 5 | 5 | L |
| 61 | 30 | 5 | 5 | 5 | 5 | 5 | 5 | L |
|  | 3 | 5 | 5 | 5 | 4 | 5 | 5 | L |
| 62 | 30 | 5 | 5 | 5 | 5 | 5 | 5 | L |
|  | 3 | 5 | 5 | 5 | 4 | 5 | 5 | N |
| 63 | 30 | 5 | 5 | 5 | 5 | 5 | 5 | L |
|  | 3 | 4 | 5 | 5 | 4 | 3 | 5 | L |
| 64 | 30 | 5 | 5 | 5 | 5 | 5 | 5 | L |
|  | 3 | 5 | 5 | 5 | 4 | 5 | 5 | L |
| 65 | 30 | 5 | 5 | 5 | 5 | 5 | 5 | L |
|  | 3 | 4 | 5 | 5 | 4 | 4 | 5 | L |
| 66 | 30 | 5 | 5 | 5 | 5 | 5 | 5 | L |
|  | 3 | 4 | 5 | 5 | 5 | 5 | 5 | L |
| 67 | 30 | 5 | 5 | 5 | 5 | 5 | 5 | L |
|  | 3 | 4 | 5 | 5 | 4 | 4 | 5 | N |
| 68 | 30 | 5 | 5 | 5 | 5 | 5 | 5 | L |
|  | 3 | 4 | 5 | 5 | 4 | 5 | 5 | L |
| 69 | 30 | 5 | 5 | 5 | 5 | 5 | 5 | L |
|  | 3 | 4 | 5 | 5 | 5 | 5 | 5 | L |
| 70 | 30 | 5 | 5 | 5 | 5 | 5 | 5 | L |
|  | 3 | 5 | 5 | 5 | 5 | 5 | 5 | L |
| 71 | 30 | 5 | 5 | 5 | 5 | 5 | 5 | L |
|  | 3 | 4 | 5 | 5 | 4 | 5 | 5 | N |
| 72 | 30 | 5 | 5 | 5 | 5 | 5 | 5 | L |
|  | 3 | 5 | 5 | 5 | 5 | 5 | 5 | L |
| 73 | 30 | 5 | 5 | 5 | 5 | 5 | 5 | L |
|  | 3 | 4 | 5 | 5 | 4 | 5 | 5 | N |
| 74 | 30 | 5 | 5 | 5 | 5 | 5 | 5 | L |
|  | 3 | 5 | 5 | 5 | 5 | 5 | 5 | L |
| 75 | 30 | 5 | 5 | 5 | 5 | 5 | 5 | L |
|  | 3 | 5 | 5 | 5 | 5 | 5 | 5 | L |
| 76 | 30 | 5 | 5 | 5 | 5 | 5 | 5 | L |
|  | 3 | 3 | 5 | 5 | 4 | 4 | 5 | N |
| 77 | 30 | 5 | 5 | 5 | 5 | 5 | 5 | L |
|  | 3 | 5 | 5 | 5 | 5 | 5 | 5 | L |
| 78 | 30 | 5 | 5 | 5 | 5 | 5 | 5 | L |
|  | 3 | 5 | 5 | 5 | 4 | 5 | 5 | L |
| 79 | 30 | 5 | 5 | 5 | 5 | 5 | 5 | L |
|  | 3 | 4 | 4 | 5 | 4 | 5 | 5 | N |
| 80 | 30 | 5 | 5 | 5 | 4 | 5 | 5 | L |
|  | 3 | 4 | 5 | 5 | 4 | 5 | 5 | N |
| 81 | 30 | 5 | 5 | 5 | 5 | 5 | 5 | L |
|  | 3 | 5 | 5 | 5 | 5 | 5 | 5 | L |
| 82 | 30 | 5 | 5 | 5 | 5 | 5 | 5 | L |
|  | 3 | 4 | 5 | 5 | 4 | 4 | 5 | L |
| 83 | 30 | 5 | 5 | 5 | 5 | 5 | 5 | L |
|  | 3 | 4 | 5 | 5 | 5 | 5 | 5 | L |
| 84 | 30 | 5 | 5 | 5 | 5 | 5 | 5 | L |
|  | 3 | 4 | 5 | 5 | 4 | 4 | 5 | N |
| 85 | 30 | 5 | 5 | 5 | 5 | 5 | 5 | L |
|  | 3 | 4 | 5 | 5 | 5 | 5 | 5 | L |
| 86 | 30 | 5 | 5 | 5 | 5 | 5 | 5 | L |
|  | 3 | 4 | 5 | 5 | 5 | 5 | 5 | L |
| 87 | 30 | 5 | 5 | 5 | 5 | 5 | 5 | L |
|  | 3 | 5 | 5 | 5 | 5 | 5 | 4 | L |
| 88 | 30 | 5 | 5 | 5 | 5 | 5 | 5 | L |
|  | 3 | 5 | 5 | 5 | 4 | 5 | 5 | L |
| 89 | 30 | 5 | 5 | 5 | 5 | 5 | 5 | L |
|  | 3 | 5 | 5 | 5 | 4 | 5 | 5 | L |
| 90 | 30 | 5 | 5 | 5 | 5 | 5 | 5 | L |
|  | 3 | 4 | 4 | 5 | 4 | 5 | 5 | L |
| 91 | 30 | 5 | 5 | 5 | 5 | 5 | 5 | L |

TABLE 3-continued

| Compound No. | Amount of active ingredient g/are | Barnyard grass | Effect of Post-emergence treatment | | | | | Crop injury Rice |
|---|---|---|---|---|---|---|---|---|
| | | | Mono-choria | Umbrella plant | Bulrush | Arrow-head | Water nutgrass | |
| | 3 | 5 | 5 | 5 | 4 | 5 | 5 | L |
| Compound A | 30 | 5 | 5 | 5 | 5 | 5 | 5 | L |
| | 3 | 2 | 4 | 4 | 2 | 3 | 2 | L |
| Compound B | 30 | 3 | 3 | 3 | 2 | 3 | 2 | N |
| | 3 | 1 | 1 | 1 | 1 | 1 | 1 | N |
| Compound C | 3 | 2 | 4 | 4 | 2 | 3 | 2 | L |

Test Example 3

Effect on upland field weeds of pre-emergence stage

Polyethylene vats, having 10×20×5 cm (depth) size, were filled with soil and seeded with oats, barnyard grass, large crabgrass, redroot pigweed, mugwort, curly dock, umbrella sedge and cocklebur, respectively, which were all upland field weeds, and the seeds were covered with soil.

The soil was treated with each active ingredient formulated to a given concentration of liquid, by spraying. After 21 days, the herbicidal effect was evaluated by comparing the results with those on the untreated plot.

The criterion for judging the herbicidal activity was the same as in Test Example 1. The results obtained are shown in Table 4.

TABLE 4

| Compound No. | Amount of active ingredient (g/are) | Effect of Pre-emergence treatment | | | | | | | |
|---|---|---|---|---|---|---|---|---|---|
| | | Oats | Barnyard grass | Large crab-grass | Redroot pigweed | Mugwort | Curly dock | Umbrella sedge | Cocklebur |
| 1 | 30 | 5 | 5 | 5 | 5 | 5 | 5 | 5 | 5 |
| | 3 | 5 | 4 | 4 | 5 | 5 | 4 | 5 | 5 |
| 2 | 30 | 5 | 5 | 5 | 5 | 5 | 5 | 5 | 5 |
| | 3 | 3 | 4 | 5 | 5 | 5 | 5 | 5 | 4 |
| 3 | 30 | 5 | 5 | 5 | 5 | 5 | 5 | 5 | 5 |
| | 3 | 3 | 4 | 5 | 5 | 5 | 5 | 5 | 5 |
| 4 | 30 | 5 | 5 | 5 | 5 | 5 | 5 | 5 | 5 |
| | 3 | 3 | 4 | 5 | 5 | 5 | 4 | 5 | 5 |
| 5 | 30 | 5 | 5 | 5 | 5 | 5 | 5 | 5 | 5 |
| | 3 | 3 | 4 | 5 | 5 | 5 | 5 | 5 | 5 |
| 6 | 30 | 5 | 5 | 5 | 5 | 5 | 5 | 5 | 5 |
| | 3 | 4 | 4 | 5 | 5 | 5 | 5 | 5 | 5 |
| 7 | 30 | 5 | 5 | 5 | 5 | 5 | 5 | 5 | 5 |
| | 3 | 3 | 4 | 5 | 5 | 5 | 5 | 5 | 5 |
| 8 | 30 | 5 | 5 | 5 | 5 | 5 | 5 | 5 | 5 |
| | 3 | 4 | 4 | 4 | 5 | 4 | 5 | 4 | 5 |
| 9 | 30 | 5 | 5 | 5 | 5 | 5 | 5 | 5 | 5 |
| | 3 | 4 | 4 | 5 | 5 | 5 | 5 | 5 | 5 |
| 10 | 30 | 5 | 5 | 5 | 5 | 5 | 5 | 5 | 5 |
| | 3 | 4 | 5 | 5 | 5 | 5 | 5 | 5 | 5 |
| 11 | 30 | 5 | 5 | 5 | 5 | 5 | 5 | 5 | 5 |
| | 3 | 4 | 4 | 5 | 5 | 5 | 4 | 5 | 5 |
| 12 | 30 | 5 | 5 | 5 | 5 | 5 | 5 | 5 | 5 |
| | 3 | 4 | 5 | 5 | 5 | 5 | 5 | 5 | 5 |
| 13 | 30 | 5 | 5 | 5 | 5 | 5 | 5 | 5 | 5 |
| | 3 | 4 | 4 | 5 | 5 | 5 | 5 | 5 | 5 |
| 14 | 30 | 5 | 5 | 5 | 5 | 5 | 5 | 5 | 5 |
| | 3 | 4 | 4 | 5 | 5 | 5 | 4 | 5 | 5 |
| 15 | 30 | 5 | 5 | 5 | 5 | 5 | 5 | 5 | 5 |
| | 3 | 5 | 5 | 5 | 5 | 5 | 5 | 5 | 5 |
| 16 | 30 | 5 | 5 | 5 | 5 | 5 | 5 | 5 | 5 |
| | 3 | 4 | 4 | 5 | 5 | 5 | 5 | 5 | 4 |
| 17 | 30 | 5 | 5 | 5 | 5 | 5 | 5 | 5 | 5 |
| | 3 | 3 | 4 | 5 | 5 | 5 | 5 | 5 | 5 |
| 18 | 30 | 5 | 5 | 5 | 5 | 5 | 5 | 5 | 5 |
| | 3 | 4 | 5 | 5 | 5 | 5 | 5 | 5 | 5 |
| 19 | 30 | 5 | 5 | 5 | 5 | 5 | 5 | 5 | 5 |
| | 3 | 4 | 4 | 5 | 5 | 5 | 5 | 5 | 5 |
| 20 | 30 | 5 | 5 | 5 | 5 | 5 | 5 | 5 | 5 |
| | 3 | 5 | 5 | 5 | 5 | 5 | 5 | 5 | 5 |
| 21 | 30 | 5 | 5 | 5 | 5 | 5 | 5 | 5 | 5 |
| | 3 | 4 | 5 | 5 | 5 | 5 | 5 | 5 | 5 |
| 22 | 30 | 5 | 5 | 5 | 5 | 5 | 5 | 5 | 5 |
| | 3 | 4 | 5 | 5 | 5 | 5 | 5 | 5 | 5 |
| 23 | 30 | 5 | 5 | 5 | 5 | 5 | 5 | 5 | 5 |
| | 3 | 3 | 4 | 5 | 5 | 5 | 4 | 5 | 4 |
| 24 | 30 | 5 | 5 | 5 | 5 | 5 | 5 | 5 | 5 |
| | 3 | 4 | 4 | 5 | 5 | 5 | 5 | 5 | 5 |
| 25 | 30 | 5 | 5 | 5 | 5 | 5 | 5 | 5 | 5 |
| | 3 | 4 | 4 | 5 | 5 | 5 | 5 | 5 | 4 |
| 26 | 30 | 5 | 5 | 5 | 5 | 5 | 5 | 5 | 5 |
| | 3 | 4 | 4 | 5 | 5 | 5 | 5 | 5 | 5 |

TABLE 4-continued

| Compound No. | Amount of active ingredient (g/are) | Effect of Pre-emergence treatment | | | | | | | |
|---|---|---|---|---|---|---|---|---|---|
| | | Oats | Barnyard grass | Large crab-grass | Redroot pigweed | Mugwort | Curly dock | Umbrella sedge | Cocklebur |
| 27 | 30 | 5 | 5 | 5 | 5 | 5 | 5 | 5 | 5 |
| | 3 | 5 | 5 | 5 | 5 | 5 | 5 | 5 | 5 |
| 28 | 30 | 5 | 5 | 5 | 5 | 5 | 5 | 5 | 5 |
| | 3 | 3 | 4 | 5 | 5 | 5 | 4 | 5 | 4 |
| 29 | 30 | 5 | 5 | 5 | 5 | 5 | 5 | 5 | 5 |
| | 3 | 4 | 5 | 5 | 5 | 5 | 5 | 5 | 5 |
| 30 | 30 | 5 | 5 | 5 | 5 | 5 | 5 | 5 | 5 |
| | 3 | 5 | 5 | 5 | 5 | 5 | 5 | 5 | 5 |
| 31 | 30 | 5 | 5 | 5 | 5 | 5 | 5 | 5 | 5 |
| | 3 | 4 | 5 | 5 | 5 | 5 | 4 | 5 | 5 |
| 32 | 30 | 5 | 5 | 5 | 5 | 5 | 5 | 5 | 5 |
| | 3 | 5 | 5 | 5 | 5 | 5 | 5 | 5 | 5 |
| 33 | 30 | 5 | 5 | 5 | 5 | 5 | 5 | 5 | 5 |
| | 3 | 5 | 5 | 5 | 5 | 5 | 5 | 5 | 5 |
| 34 | 30 | 5 | 5 | 5 | 5 | 5 | 5 | 5 | 5 |
| | 3 | 4 | 5 | 5 | 5 | 5 | 5 | 5 | 5 |
| 35 | 30 | 5 | 5 | 5 | 5 | 5 | 5 | 5 | 5 |
| | 3 | 4 | 4 | 5 | 5 | 5 | 4 | 5 | 5 |
| 36 | 30 | 5 | 5 | 5 | 5 | 5 | 5 | 5 | 5 |
| | 3 | 4 | 4 | 5 | 5 | 5 | 5 | 5 | 5 |
| 37 | 30 | 5 | 5 | 5 | 5 | 5 | 5 | 5 | 5 |
| | 3 | 5 | 5 | 5 | 5 | 5 | 5 | 5 | 5 |
| 38 | 30 | 5 | 5 | 5 | 5 | 5 | 5 | 5 | 5 |
| | 3 | 3 | 4 | 5 | 5 | 5 | 4 | 5 | 5 |
| 39 | 30 | 5 | 5 | 5 | 5 | 5 | 5 | 5 | 5 |
| | 3 | 5 | 5 | 5 | 5 | 5 | 5 | 5 | 5 |
| 40 | 30 | 5 | 5 | 5 | 5 | 5 | 5 | 5 | 5 |
| | 3 | 4 | 5 | 5 | 5 | 5 | 5 | 5 | 5 |
| 41 | 30 | 5 | 5 | 5 | 5 | 5 | 5 | 5 | 5 |
| | 3 | 4 | 5 | 5 | 5 | 5 | 5 | 5 | 5 |
| 42 | 30 | 5 | 5 | 5 | 5 | 5 | 5 | 5 | 5 |
| | 3 | 4 | 5 | 5 | 5 | 5 | 5 | 5 | 5 |
| 43 | 30 | 5 | 5 | 5 | 5 | 5 | 5 | 5 | 5 |
| | 3 | 4 | 4 | 5 | 5 | 5 | 5 | 5 | 5 |
| 44 | 30 | 5 | 5 | 5 | 5 | 5 | 5 | 5 | 5 |
| | 3 | 4 | 4 | 5 | 5 | 5 | 5 | 5 | 5 |
| 45 | 30 | 5 | 5 | 5 | 5 | 5 | 5 | 5 | 5 |
| | 3 | 5 | 5 | 5 | 5 | 5 | 5 | 5 | 5 |
| 46 | 30 | 5 | 5 | 5 | 5 | 5 | 5 | 5 | 5 |
| | 3 | 4 | 5 | 5 | 5 | 5 | 5 | 5 | 5 |
| 47 | 30 | 5 | 5 | 5 | 5 | 5 | 5 | 5 | 5 |
| | 3 | 4 | 4 | 4 | 5 | 5 | 5 | 5 | 5 |
| 48 | 30 | 5 | 5 | 5 | 5 | 5 | 5 | 5 | 5 |
| | 3 | 4 | 5 | 5 | 5 | 5 | 5 | 5 | 5 |
| 49 | 30 | 5 | 5 | 5 | 5 | 5 | 5 | 5 | 5 |
| | 3 | 3 | 5 | 5 | 5 | 5 | 5 | 5 | 5 |
| 50 | 30 | 5 | 5 | 5 | 5 | 5 | 5 | 5 | 5 |
| | 3 | 4 | 4 | 5 | 5 | 5 | 5 | 5 | 5 |
| 51 | 30 | 5 | 5 | 5 | 5 | 5 | 5 | 5 | 5 |
| | 3 | 3 | 4 | 5 | 5 | 5 | 5 | 5 | 5 |
| 52 | 30 | 5 | 5 | 5 | 5 | 5 | 5 | 5 | 5 |
| | 3 | 5 | 5 | 5 | 5 | 5 | 5 | 5 | 5 |
| 53 | 30 | 5 | 5 | 5 | 5 | 5 | 5 | 5 | 5 |
| | 3 | 4 | 5 | 5 | 5 | 5 | 5 | 5 | 4 |
| 54 | 30 | 5 | 5 | 5 | 5 | 5 | 5 | 5 | 5 |
| | 3 | 5 | 5 | 5 | 5 | 5 | 5 | 5 | 5 |
| 55 | 30 | 5 | 5 | 5 | 5 | 5 | 5 | 5 | 5 |
| | 3 | 5 | 5 | 5 | 5 | 5 | 5 | 5 | 5 |
| 56 | 30 | 5 | 5 | 5 | 5 | 5 | 5 | 5 | 5 |
| | 3 | 4 | 4 | 5 | 5 | 5 | 5 | 5 | 5 |
| 57 | 30 | 5 | 5 | 5 | 5 | 5 | 5 | 5 | 5 |
| | 3 | 5 | 5 | 5 | 5 | 5 | 5 | 5 | 5 |
| 58 | 30 | 5 | 5 | 5 | 5 | 5 | 5 | 5 | 5 |
| | 3 | 4 | 5 | 5 | 5 | 5 | 5 | 4 | 5 |
| 59 | 30 | 5 | 5 | 5 | 5 | 5 | 5 | 5 | 5 |
| | 3 | 5 | 5 | 5 | 5 | 5 | 5 | 5 | 5 |
| 60 | 30 | 5 | 5 | 5 | 5 | 5 | 5 | 5 | 5 |
| | 3 | 5 | 5 | 5 | 5 | 5 | 5 | 5 | 5 |
| 61 | 30 | 5 | 5 | 5 | 5 | 5 | 5 | 5 | 5 |
| | 3 | 4 | 4 | 5 | 5 | 5 | 5 | 5 | 5 |
| 62 | 30 | 5 | 5 | 5 | 5 | 5 | 5 | 5 | 5 |
| | 3 | 5 | 5 | 5 | 5 | 5 | 5 | 5 | 5 |
| 63 | 30 | 5 | 5 | 5 | 5 | 5 | 5 | 5 | 5 |
| | 3 | 4 | 4 | 5 | 5 | 5 | 4 | 5 | 4 |
| 64 | 30 | 5 | 5 | 5 | 5 | 5 | 5 | 5 | 5 |
| | 3 | 5 | 5 | 5 | 5 | 5 | 5 | 5 | 5 |
| 65 | 30 | 5 | 5 | 5 | 5 | 5 | 5 | 5 | 5 |
| | 3 | 4 | 4 | 5 | 5 | 5 | 5 | 5 | 5 |

TABLE 4-continued

| Compound No. | Amount of active ingredient (g/are) | Effect of Pre-emergence treatment | | | | | | | |
|---|---|---|---|---|---|---|---|---|---|
| | | Oats | Barnyard grass | Large crab-grass | Redroot pigweed | Mugwort | Curly dock | Umbrella sedge | Cocklebur |
| 66 | 30 | 5 | 5 | 5 | 5 | 5 | 5 | 5 | 5 |
|    | 3  | 4 | 5 | 5 | 5 | 5 | 5 | 5 | 5 |
| 67 | 30 | 5 | 5 | 5 | 5 | 5 | 5 | 5 | 5 |
|    | 3  | 4 | 4 | 5 | 5 | 5 | 5 | 5 | 4 |
| 68 | 30 | 5 | 5 | 5 | 5 | 5 | 5 | 5 | 5 |
|    | 3  | 5 | 5 | 5 | 5 | 5 | 5 | 5 | 5 |
| 69 | 30 | 5 | 5 | 5 | 5 | 5 | 5 | 5 | 5 |
|    | 3  | 5 | 5 | 5 | 5 | 5 | 5 | 5 | 5 |
| 70 | 30 | 5 | 5 | 5 | 5 | 5 | 5 | 5 | 5 |
|    | 3  | 4 | 4 | 5 | 5 | 5 | 5 | 5 | 5 |
| 71 | 30 | 5 | 5 | 5 | 5 | 5 | 5 | 5 | 5 |
|    | 3  | 4 | 4 | 5 | 5 | 5 | 5 | 5 | 5 |
| 72 | 30 | 5 | 5 | 5 | 5 | 5 | 5 | 5 | 5 |
|    | 3  | 5 | 5 | 5 | 5 | 5 | 5 | 5 | 5 |
| 73 | 30 | 5 | 5 | 5 | 5 | 5 | 5 | 5 | 5 |
|    | 3  | 4 | 5 | 5 | 5 | 5 | 5 | 5 | 5 |
| 74 | 30 | 5 | 5 | 5 | 5 | 5 | 5 | 5 | 5 |
|    | 3  | 5 | 5 | 5 | 5 | 5 | 5 | 5 | 5 |
| 75 | 30 | 5 | 5 | 5 | 5 | 5 | 5 | 5 | 5 |
|    | 3  | 5 | 5 | 5 | 5 | 5 | 5 | 5 | 5 |
| 76 | 30 | 5 | 5 | 5 | 5 | 5 | 5 | 5 | 5 |
|    | 3  | 4 | 5 | 5 | 5 | 5 | 5 | 5 | 4 |
| 77 | 30 | 5 | 5 | 5 | 5 | 5 | 5 | 5 | 5 |
|    | 3  | 5 | 5 | 5 | 5 | 5 | 5 | 5 | 5 |
| 78 | 30 | 5 | 5 | 5 | 5 | 5 | 5 | 5 | 5 |
|    | 3  | 5 | 5 | 5 | 5 | 5 | 5 | 5 | 5 |
| 79 | 30 | 5 | 5 | 5 | 5 | 5 | 5 | 5 | 5 |
|    | 3  | 4 | 4 | 5 | 5 | 5 | 4 | 5 | 5 |
| 80 | 30 | 5 | 5 | 5 | 5 | 5 | 5 | 5 | 5 |
|    | 3  | 4 | 5 | 5 | 5 | 5 | 5 | 5 | 5 |
| 81 | 30 | 5 | 5 | 5 | 5 | 5 | 5 | 5 | 5 |
|    | 3  | 4 | 4 | 5 | 5 | 5 | 5 | 5 | 5 |
| 82 | 30 | 5 | 5 | 5 | 5 | 5 | 5 | 5 | 5 |
|    | 3  | 4 | 5 | 5 | 5 | 5 | 5 | 5 | 5 |
| 83 | 30 | 5 | 5 | 5 | 5 | 5 | 5 | 5 | 5 |
|    | 3  | 4 | 4 | 5 | 5 | 5 | 5 | 5 | 5 |
| 84 | 30 | 5 | 5 | 5 | 5 | 5 | 5 | 5 | 5 |
|    | 3  | 5 | 5 | 5 | 5 | 5 | 5 | 5 | 5 |
| 85 | 30 | 5 | 5 | 5 | 5 | 5 | 5 | 5 | 5 |
|    | 3  | 4 | 5 | 5 | 5 | 5 | 4 | 5 | 5 |
| 86 | 30 | 5 | 5 | 5 | 5 | 5 | 5 | 5 | 5 |
|    | 3  | 3 | 4 | 5 | 5 | 5 | 5 | 5 | 5 |
| 87 | 30 | 5 | 5 | 5 | 5 | 5 | 5 | 5 | 5 |
|    | 3  | 5 | 5 | 5 | 5 | 5 | 5 | 5 | 5 |
| 88 | 30 | 5 | 5 | 5 | 5 | 5 | 5 | 5 | 5 |
|    | 3  | 4 | 5 | 5 | 5 | 5 | 5 | 5 | 5 |
| 89 | 30 | 5 | 5 | 5 | 5 | 5 | 5 | 5 | 5 |
|    | 3  | 5 | 5 | 5 | 5 | 5 | 5 | 5 | 5 |
| 90 | 30 | 5 | 5 | 5 | 5 | 5 | 5 | 5 | 5 |
|    | 3  | 4 | 4 | 5 | 5 | 5 | 4 | 5 | 5 |
| 91 | 30 | 5 | 5 | 5 | 5 | 5 | 5 | 5 | 5 |
|    | 3  | 5 | 5 | 5 | 5 | 5 | 5 | 5 | 5 |
| Compound A | 30 | 2 | 4 | 4 | 5 | 5 | 5 | 5 | 4 |
|            | 3  | 1 | 2 | 3 | 5 | 4 | 3 | 4 | 2 |
| Compound B | 30 | 2 | 2 | 4 | 5 | 5 | 4 | 5 | 3 |
|            | 3  | 1 | 1 | 2 | 4 | 3 | 2 | 5 | 1 |
| Compound C | 3  | 2 | 3 | 3 | 5 | 4 | 3 | 4 | 1 |

Test Example 4

Effect on upland field weeds of post-emergence stage

Polyethylene vats, having 10×20×5 cm (depth) size, were filled with soil and seeded with the injurious weeds shown below and soybean seeds, respectively, and the seeds were covered with soil. The weeds and soybean were cultivated respectively to the following leaf ages and then treated with each active ingredient at a given dosage.

After 21 days, the herbicidal effect on the weeds and the degree of corp injury to the soybean were evaluated by comparing the results with those on the untreated plot.

| Species of test plant | Leaf age |
|---|---|
| Oats | 2 |
| Large crabgrass | 2 |
| Redroot pigweed | 1 |
| Mugwort | 1 |
| Curly dock | 2 |
| Umbrella sedge | 1 |
| Cocklebur | 1 |
| Soybean | First trifoliate age |

The criteria for judging the herbicidal activity and crop injury were the same as in Test Examples 1 and 2, respectively. The results obtained are shown in Table 5.

TABLE 5

| Compound No. | Amount of active ingredient (g/are) | Herbicidal effect of post-emergence treatment | | | | | | | Crop injury Soybean |
|---|---|---|---|---|---|---|---|---|---|
| | | Oats | Large crab-grass | Redroot pigweed | Mug-wort | Curly dock | Umbrella sedge | Cock-lebur | |
| 1 | 30 | 5 | 5 | 5 | 5 | 5 | 5 | 5 | N |
| | 3 | 3 | 3 | 5 | 5 | 4 | 5 | 4 | N |
| 2 | 30 | 5 | 5 | 5 | 5 | 5 | 5 | 5 | N |
| | 3 | 3 | 4 | 5 | 5 | 5 | 5 | 5 | N |
| 3 | 30 | 5 | 5 | 5 | 5 | 5 | 5 | 5 | N |
| | 3 | 4 | 5 | 5 | 5 | 5 | 5 | 5 | N |
| 4 | 30 | 5 | 5 | 5 | 5 | 5 | 5 | 5 | N |
| | 3 | 3 | 4 | 4 | 5 | 5 | 5 | 5 | N |
| 5 | 30 | 5 | 5 | 5 | 5 | 5 | 5 | 5 | N |
| | 3 | 3 | 4 | 5 | 5 | 4 | 5 | 4 | N |
| 6 | 30 | 5 | 5 | 5 | 5 | 5 | 5 | 5 | N |
| | 3 | 4 | 4 | 5 | 5 | 4 | 5 | 5 | N |
| 7 | 30 | 5 | 5 | 5 | 5 | 5 | 5 | 5 | L |
| | 3 | 4 | 5 | 5 | 5 | 5 | 5 | 4 | N |
| 8 | 30 | 5 | 5 | 5 | 5 | 5 | 5 | 5 | N |
| | 3 | 4 | 4 | 5 | 5 | 5 | 5 | 4 | N |
| 9 | 30 | 5 | 5 | 5 | 5 | 5 | 5 | 5 | N |
| | 3 | 4 | 4 | 5 | 5 | 4 | 5 | 5 | N |
| 10 | 30 | 5 | 5 | 5 | 5 | 5 | 5 | 5 | N |
| | 3 | 4 | 4 | 5 | 5 | 5 | 5 | 4 | N |
| 11 | 30 | 5 | 5 | 5 | 5 | 5 | 5 | 5 | L |
| | 3 | 4 | 5 | 5 | 5 | 5 | 5 | 5 | N |
| 12 | 30 | 5 | 5 | 5 | 5 | 5 | 5 | 5 | N |
| | 3 | 4 | 4 | 5 | 5 | 5 | 5 | 4 | N |
| 13 | 30 | 5 | 5 | 5 | 5 | 5 | 5 | 5 | L |
| | 3 | 4 | 5 | 5 | 5 | 5 | 5 | 5 | N |
| 14 | 30 | 5 | 5 | 5 | 5 | 5 | 5 | 5 | N |
| | 3 | 4 | 4 | 5 | 5 | 5 | 5 | 5 | N |
| 15 | 30 | 5 | 5 | 5 | 5 | 5 | 5 | 5 | L |
| | 3 | 5 | 5 | 5 | 5 | 5 | 5 | 5 | N |
| 16 | 30 | 5 | 5 | 5 | 5 | 5 | 5 | 5 | N |
| | 3 | 4 | 5 | 5 | 5 | 5 | 5 | 5 | N |
| 17 | 30 | 5 | 5 | 5 | 5 | 5 | 5 | 5 | N |
| | 3 | 4 | 4 | 5 | 5 | 5 | 5 | 5 | N |
| 18 | 30 | 5 | 5 | 5 | 5 | 5 | 5 | 5 | L |
| | 3 | 4 | 5 | 5 | 5 | 5 | 5 | 5 | N |
| 19 | 30 | 5 | 5 | 5 | 5 | 5 | 5 | 5 | N |
| | 3 | 4 | 4 | 5 | 5 | 5 | 5 | 5 | N |
| 20 | 30 | 5 | 5 | 5 | 5 | 5 | 5 | 5 | L |
| | 3 | 5 | 5 | 5 | 5 | 5 | 5 | 5 | N |
| 21 | 30 | 5 | 5 | 5 | 5 | 5 | 5 | 5 | N |
| | 3 | 5 | 5 | 5 | 5 | 5 | 5 | 5 | N |
| 22 | 30 | 5 | 5 | 5 | 5 | 5 | 5 | 5 | L |
| | 3 | 4 | 5 | 5 | 5 | 5 | 5 | 5 | N |
| 23 | 30 | 5 | 5 | 5 | 5 | 5 | 5 | 5 | L |
| | 3 | 5 | 5 | 5 | 5 | 5 | 5 | 5 | N |
| 24 | 30 | 5 | 5 | 5 | 5 | 5 | 5 | 5 | L |
| | 3 | 4 | 5 | 5 | 5 | 5 | 5 | 5 | N |
| 25 | 30 | 5 | 5 | 5 | 5 | 5 | 5 | 5 | N |
| | 3 | 4 | 4 | 5 | 5 | 5 | 5 | 5 | N |
| 26 | 30 | 5 | 5 | 5 | 5 | 5 | 5 | 5 | N |
| | 3 | 4 | 4 | 5 | 5 | 5 | 5 | 5 | N |
| 27 | 30 | 5 | 5 | 5 | 5 | 5 | 5 | 5 | L |
| | 3 | 5 | 5 | 5 | 5 | 5 | 5 | 5 | N |
| 28 | 30 | 5 | 5 | 5 | 5 | 5 | 5 | 5 | L |
| | 3 | 3 | 4 | 5 | 5 | 4 | 5 | 5 | N |
| 29 | 30 | 5 | 5 | 5 | 5 | 5 | 5 | 5 | L |
| | 3 | 5 | 5 | 5 | 5 | 5 | 5 | 5 | N |
| 30 | 30 | 5 | 5 | 5 | 5 | 5 | 5 | 5 | N |
| | 3 | 5 | 5 | 5 | 5 | 5 | 5 | 5 | N |
| 31 | 30 | 5 | 5 | 5 | 5 | 5 | 5 | 5 | N |
| | 3 | 4 | 4 | 5 | 5 | 5 | 5 | 5 | N |
| 32 | 30 | 5 | 5 | 5 | 5 | 5 | 5 | 5 | L |
| | 3 | 5 | 5 | 5 | 5 | 5 | 5 | 5 | N |
| 33 | 30 | 5 | 5 | 5 | 5 | 5 | 5 | 5 | N |
| | 3 | 4 | 5 | 5 | 5 | 5 | 5 | 5 | N |
| 34 | 30 | 5 | 5 | 5 | 5 | 5 | 5 | 5 | L |
| | 3 | 5 | 5 | 5 | 5 | 5 | 5 | 5 | N |
| 35 | 30 | 5 | 5 | 5 | 5 | 5 | 5 | 5 | L |
| | 3 | 4 | 5 | 5 | 5 | 4 | 5 | 5 | N |
| 36 | 30 | 5 | 5 | 5 | 5 | 5 | 5 | 5 | N |
| | 3 | 4 | 4 | 5 | 5 | 5 | 5 | 5 | N |
| 37 | 30 | 5 | 5 | 5 | 5 | 5 | 5 | 5 | N |
| | 3 | 4 | 5 | 5 | 5 | 5 | 5 | 5 | N |
| 38 | 30 | 5 | 5 | 5 | 5 | 5 | 5 | 5 | L |
| | 3 | 4 | 4 | 5 | 5 | 4 | 5 | 5 | N |
| 39 | 30 | 5 | 5 | 5 | 5 | 5 | 5 | 5 | L |
| | 3 | 5 | 5 | 5 | 5 | 5 | 5 | 5 | N |

TABLE 5-continued

| Compound No. | Amount of active ingredient (g/are) | Herbicidal effect of post-emergence treatment | | | | | | | Crop injury Soybean |
|---|---|---|---|---|---|---|---|---|---|
| | | Oats | Large crab-grass | Redroot pigweed | Mug-wort | Curly dock | Umbrella sedge | Cock-lebur | |
| 40 | 30 | 5 | 5 | 5 | 5 | 5 | 5 | 5 | N |
| | 3 | 3 | 4 | 5 | 5 | 5 | 5 | 5 | N |
| 41 | 30 | 5 | 5 | 5 | 5 | 5 | 5 | 5 | N |
| | 3 | 4 | 5 | 5 | 5 | 5 | 5 | 5 | N |
| 42 | 30 | 5 | 5 | 5 | 5 | 5 | 5 | 5 | N |
| | 3 | 4 | 5 | 5 | 5 | 5 | 5 | 5 | N |
| 43 | 30 | 5 | 5 | 5 | 5 | 5 | 5 | 5 | N |
| | 3 | 5 | 5 | 5 | 5 | 5 | 5 | 5 | N |
| 44 | 30 | 5 | 5 | 5 | 5 | 5 | 5 | 5 | N |
| | 3 | 4 | 4 | 5 | 5 | 5 | 5 | 5 | N |
| 45 | 30 | 5 | 5 | 5 | 5 | 5 | 5 | 5 | L |
| | 3 | 4 | 5 | 5 | 5 | 5 | 5 | 5 | N |
| 46 | 30 | 5 | 5 | 5 | 5 | 5 | 5 | 5 | N |
| | 3 | 4 | 5 | 5 | 5 | 5 | 5 | 5 | N |
| 47 | 30 | 5 | 5 | 5 | 5 | 5 | 5 | 5 | N |
| | 3 | 4 | 4 | 5 | 5 | 4 | 5 | 5 | N |
| 48 | 30 | 5 | 5 | 5 | 5 | 5 | 5 | 5 | L |
| | 3 | 4 | 4 | 5 | 5 | 5 | 5 | 5 | N |
| 49 | 30 | 5 | 5 | 5 | 5 | 5 | 5 | 5 | L |
| | 3 | 5 | 5 | 5 | 5 | 5 | 5 | 5 | N |
| 50 | 30 | 5 | 5 | 5 | 5 | 5 | 5 | 5 | L |
| | 3 | 4 | 4 | 5 | 5 | 5 | 5 | 5 | N |
| 51 | 30 | 5 | 5 | 5 | 5 | 5 | 5 | 5 | L |
| | 3 | 5 | 5 | 5 | 5 | 5 | 5 | 5 | N |
| 52 | 30 | 5 | 5 | 5 | 5 | 5 | 5 | 5 | L |
| | 3 | 5 | 5 | 5 | 5 | 5 | 5 | 5 | N |
| 53 | 30 | 5 | 5 | 5 | 5 | 5 | 5 | 5 | L |
| | 3 | 5 | 5 | 5 | 5 | 5 | 5 | 5 | N |
| 54 | 30 | 5 | 5 | 5 | 5 | 5 | 5 | 5 | L |
| | 3 | 5 | 5 | 5 | 5 | 5 | 5 | 5 | L |
| 55 | 30 | 5 | 5 | 5 | 5 | 5 | 5 | 5 | L |
| | 3 | 5 | 5 | 5 | 5 | 5 | 5 | 5 | N |
| 56 | 30 | 5 | 5 | 5 | 5 | 5 | 5 | 5 | N |
| | 3 | 3 | 4 | 5 | 5 | 5 | 5 | 5 | N |
| 57 | 30 | 5 | 5 | 5 | 5 | 5 | 5 | 5 | L |
| | 3 | 4 | 5 | 5 | 5 | 5 | 5 | 5 | N |
| 58 | 30 | 5 | 5 | 5 | 5 | 5 | 5 | 5 | L |
| | 3 | 5 | 5 | 5 | 5 | 5 | 5 | 5 | L |
| 59 | 30 | 5 | 5 | 5 | 5 | 5 | 5 | 5 | L |
| | 3 | 4 | 5 | 5 | 5 | 5 | 5 | 5 | N |
| 60 | 30 | 5 | 5 | 5 | 5 | 5 | 5 | 5 | N |
| | 3 | 5 | 5 | 5 | 5 | 5 | 5 | 5 | N |
| 61 | 30 | 5 | 5 | 5 | 5 | 5 | 5 | 5 | L |
| | 3 | 5 | 5 | 5 | 5 | 5 | 5 | 5 | N |
| 62 | 30 | 5 | 5 | 5 | 5 | 5 | 5 | 5 | L |
| | 3 | 4 | 5 | 5 | 5 | 5 | 5 | 5 | N |
| 63 | 30 | 5 | 5 | 5 | 5 | 5 | 5 | 5 | L |
| | 3 | 4 | 4 | 5 | 5 | 4 | 5 | 5 | N |
| 64 | 30 | 5 | 5 | 5 | 5 | 5 | 5 | 5 | L |
| | 3 | 5 | 5 | 5 | 5 | 5 | 5 | 5 | N |
| 65 | 30 | 5 | 5 | 5 | 5 | 5 | 5 | 5 | L |
| | 3 | 4 | 4 | 5 | 5 | 5 | 5 | 5 | N |
| 66 | 30 | 5 | 5 | 5 | 5 | 5 | 5 | 5 | L |
| | 3 | 5 | 5 | 5 | 5 | 5 | 5 | 5 | N |
| 67 | 30 | 5 | 5 | 5 | 5 | 5 | 5 | 5 | N |
| | 3 | 4 | 4 | 5 | 5 | 4 | 5 | 5 | N |
| 68 | 30 | 5 | 5 | 5 | 5 | 5 | 5 | 5 | L |
| | 3 | 4 | 4 | 5 | 5 | 5 | 5 | 5 | N |
| 69 | 30 | 5 | 5 | 5 | 5 | 5 | 5 | 5 | N |
| | 3 | 5 | 5 | 5 | 5 | 5 | 5 | 5 | N |
| 70 | 30 | 5 | 5 | 5 | 5 | 5 | 5 | 5 | N |
| | 3 | 4 | 4 | 5 | 5 | 5 | 5 | 5 | N |
| 71 | 30 | 5 | 5 | 5 | 5 | 5 | 5 | 5 | N |
| | 3 | 3 | 4 | 5 | 5 | 4 | 5 | 5 | N |
| 72 | 30 | 5 | 5 | 5 | 5 | 5 | 5 | 5 | L |
| | 3 | 4 | 5 | 5 | 5 | 5 | 5 | 5 | N |
| 73 | 30 | 5 | 5 | 5 | 5 | 5 | 5 | 5 | N |
| | 3 | 4 | 4 | 5 | 5 | 5 | 5 | 5 | N |
| 74 | 30 | 5 | 5 | 5 | 5 | 5 | 5 | 5 | L |
| | 3 | 4 | 4 | 5 | 5 | 5 | 5 | 5 | N |
| 75 | 30 | 5 | 5 | 5 | 5 | 5 | 5 | 5 | L |
| | 3 | 4 | 5 | 5 | 5 | 5 | 5 | 5 | N |
| 76 | 30 | 5 | 5 | 5 | 5 | 5 | 5 | 5 | L |
| | 3 | 5 | 5 | 5 | 5 | 5 | 5 | 5 | N |
| 77 | 30 | 5 | 5 | 5 | 5 | 5 | 5 | 5 | L |
| | 3 | 5 | 5 | 5 | 5 | 5 | 5 | 5 | N |
| 78 | 30 | 5 | 5 | 5 | 5 | 5 | 5 | 5 | N |
| | 3 | 5 | 5 | 5 | 5 | 5 | 5 | 5 | N |

TABLE 5-continued

| Compound No. | Amount of active ingredient (g/are) | Herbicidal effect of post-emergence treatment | | | | | | | Crop injury Soybean |
|---|---|---|---|---|---|---|---|---|---|
| | | Oats | Large crab-grass | Redroot pigweed | Mug-wort | Curly dock | Umbrella sedge | Cock-lebur | |
| 79 | 30 | 5 | 5 | 5 | 5 | 5 | 5 | 5 | L |
| | 3 | 4 | 4 | 5 | 5 | 5 | 5 | 5 | N |
| 80 | 30 | 5 | 5 | 5 | 5 | 5 | 5 | 5 | N |
| | 3 | 4 | 4 | 5 | 5 | 5 | 4 | 5 | N |
| 81 | 30 | 5 | 5 | 5 | 5 | 5 | 5 | 5 | N |
| | 3 | 4 | 4 | 5 | 5 | 5 | 5 | 5 | N |
| 82 | 30 | 5 | 5 | 5 | 5 | 5 | 5 | 5 | L |
| | 3 | 4 | 5 | 5 | 5 | 5 | 5 | 5 | N |
| 83 | 30 | 5 | 5 | 5 | 5 | 5 | 5 | 5 | N |
| | 3 | 4 | 5 | 5 | 5 | 5 | 5 | 5 | N |
| 84 | 30 | 5 | 5 | 5 | 5 | 5 | 5 | 5 | N |
| | 3 | 5 | 5 | 5 | 5 | 5 | 5 | 5 | N |
| 85 | 30 | 5 | 5 | 5 | 5 | 5 | 5 | 5 | N |
| | 3 | 4 | 5 | 5 | 5 | 5 | 5 | 5 | N |
| 86 | 30 | 5 | 5 | 5 | 5 | 5 | 5 | 5 | N |
| | 3 | 3 | 4 | 5 | 5 | 5 | 5 | 5 | N |
| 87 | 30 | 5 | 5 | 5 | 5 | 5 | 5 | 5 | N |
| | 3 | 5 | 4 | 5 | 5 | 5 | 5 | 5 | N |
| 88 | 30 | 5 | 5 | 5 | 5 | 5 | 5 | 5 | N |
| | 3 | 4 | 5 | 5 | 5 | 5 | 5 | 5 | N |
| 89 | 30 | 5 | 5 | 5 | 5 | 5 | 5 | 5 | N |
| | 3 | 4 | 4 | 5 | 5 | 5 | 5 | 5 | N |
| 90 | 30 | 5 | 5 | 5 | 5 | 5 | 5 | 5 | N |
| | 3 | 3 | 4 | 5 | 5 | 5 | 5 | 5 | N |
| 91 | 30 | 5 | 5 | 5 | 5 | 5 | 5 | 5 | N |
| | 3 | 4 | 5 | 5 | 5 | 5 | 5 | 5 | N |
| Compound A | 30 | 3 | 5 | 5 | 5 | 5 | 5 | 4 | L |
| | 3 | 2 | 3 | 4 | 3 | 3 | 3 | 2 | L |
| Compound B | 30 | 4 | 2 | 5 | 4 | 4 | 5 | 4 | N |
| | 3 | 1 | 1 | 3 | 3 | 1 | 1 | 1 | N |
| Compound C | 3 | 2 | 3 | 4 | 3 | 2 | 3 | 2 | L |

Preparation Example 1

A wettable powder composition was prepared by mixing uniformly and grinding the following ingredients:

| | |
|---|---|
| Compound No. 1 | 50 Parts |
| Mixture of Clay and white carbon (in which clay is contained as the major component) | 45 Parts |
| Polyoxyethylene nonylphenyl ether | 5 Parts |

Preparation Example 2

A granular composition was prepared by mixing uniformly and grinding the following ingredients, sufficiently kneading the mixture with a suitable amount of water, and granulating the kneaded mixture:

| | |
|---|---|
| Compound No. 7 | 5 Parts |
| Mixture of bentonite and clay | 90 Parts |
| Calcium ligninsulfonate | 5 Parts |

Preparation Example 3

An emulsifiable concentrate was prepared by mixing uniformly the following ingredients:

| | |
|---|---|
| Compound No. 31 | 50 Parts |
| Xylene | 40 Parts |
| Mixture of polyoxyethylene nonylphenyl ether and | 10 Parts |

| -continued | |
|---|---|
| calcium alkylbenzenesulfonate | |

What is claimed is:

1. A $\Delta^2$-1,2,4-triazolin-5-one derivative represented by the general formula (I):

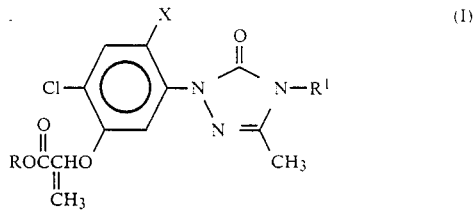

wherein R is an alkoxyalkoxyalkyl group having 3 to 8 carbon atoms; $R^1$ is $CF_2CHF_2$; and X is a fluorine atom.

2. a herbicidal composition comprising an effective amount of a $\Delta^2$-1,2,4-triazolin-5-one derivative as an active ingredient and a suitable inert carrier, said $\Delta^2$-1,2,4-triazolin-5-one derivative being represented by the general formula (I):

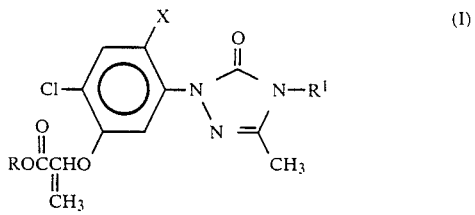

wherein R is an alkoxyalkoxyalkyl group having 3 to 8 carbon atoms; $R^1$ is $CF_2CHF_2$ and X is a fluorine atom.

3. A derivative according to claim 1 wherein R is $CH_3O(CH_2)_2O(CH_2)_2$—.

4. A herbicidal composition according to claim 2, wherein the active ingredient has R being $CH_3O(CH_2)_2O(CH_2)_2$—.

5. A method for the control of weeds in upland fields, which comprises applying to said upland fields a weed-destroying or weed-growth inhibiting dosage of the herbicidal composition of claim 2.

6. A method for the control of weeds in upland fields, which comprises applying to said upland fields a weed-destroying or weed-growth inhibiting dosage of the herbicidal composition of claim 4.

7. A method for the pre-emergent control of weeds in upland fields, which comprises applying to said upland fields a weed-growth inhibiting amount of the herbicidal composition of claim 2.

8. A method for the pre-emergent control of weeds in upland fields, which comprises applying to said upland fields a weed-growth inhibiting amount of the herbicidal composition of claim 4.

9. A method for the post-emergent control of weeds in upland fields, which comprises applying to said upland fields a weed-destroying amount of herbicidal composition of claim 2.

10. A method for the post-emergent control of weeds in upland fields, which comprises applying to said upland fields a weed-destroying amount of the herbicidal composition of claim 4.

11. A method for the pre-emergent control of weeds in upland fields containing soybeans, which comprises applying to said upland fields weed-growth inhibiting amount of the herbicidal composition of claim 2.

12. A method for the pre-emergent control of weeds in upland field containing soybeans, which comprises applying to said upland fields a weed-growth inhibiting amount of the herbicidal composition of claim 4.

13. A method for the post-emergent control of weeds in upland fields containing soybeans, which comprises applying to said upland fields a weed-destroying amount of the herbicidal composition of claim 2.

14. A method for the post-emergent control of weeds in upland fields containing soybeans, which comprises applying to said upland fields a weed-destroying amount of the herbicidal composition of claim 4.

* * * * *